(12) United States Patent
Murphy

(10) Patent No.: US 11,142,498 B2
(45) Date of Patent: Oct. 12, 2021

(54) KERATIN DYEING COMPOUNDS, COMPOSITIONS CONTAINING THEM, AND METHOD AND USE THEREOF

(71) Applicant: Noxell Corporation, Hunt Valley, MD (US)

(72) Inventor: Bryan P. Murphy, Loveland, OH (US)

(73) Assignee: WELLA OPERATIONS US, LLC, Calabasas, CA (US)

(*) Notice: Subject to any disclaimer, the term of this patent is extended or adjusted under 35 U.S.C. 154(b) by 0 days.

(21) Appl. No.: 16/754,707

(22) PCT Filed: Oct. 3, 2018

(86) PCT No.: PCT/US2018/054106
§ 371 (c)(1),
(2) Date: Apr. 8, 2020

(87) PCT Pub. No.: WO2019/074736
PCT Pub. Date: Apr. 18, 2019

(65) Prior Publication Data
US 2020/0247749 A1    Aug. 6, 2020

Related U.S. Application Data

(60) Provisional application No. 62/572,020, filed on Oct. 13, 2017.

(51) Int. Cl.
*A61Q 5/10* (2006.01)
*C07D 209/30* (2006.01)
*A61K 8/41* (2006.01)
*A61K 8/49* (2006.01)
*C07D 403/06* (2006.01)

(52) U.S. Cl.
CPC .......... *C07D 209/30* (2013.01); *A61K 8/411* (2013.01); *A61K 8/415* (2013.01); *A61K 8/492* (2013.01); *A61K 8/4946* (2013.01); *A61Q 5/10* (2013.01); *C07D 403/06* (2013.01); *A61K 2800/4324* (2013.01); *A61K 2800/88* (2013.01)

(58) Field of Classification Search
CPC .......... A61Q 5/10; A61Q 5/065; A61K 8/411; A61K 8/4926; A61K 8/415; A61K 8/49; A61K 2800/88; A61K 2800/4324; A61K 8/492; C07D 209/30; C07D 403/06

USPC .......................................................... 8/405
See application file for complete search history.

(56) References Cited

U.S. PATENT DOCUMENTS

| | | | | |
|---|---|---|---|---|
| 4,776,857 A * | 10/1988 | Carroll | ..................... | A61Q 5/10 8/423 |
| 5,538,517 A | 7/1996 | Samain et al. | | |
| 5,609,649 A | 3/1997 | Junino et al. | | |
| 7,060,109 B2 * | 6/2006 | Hoeffkes | ............... | A61K 8/4973 8/405 |
| 7,247,173 B2 * | 7/2007 | Kleen | ..................... | A61K 8/411 8/405 |
| 8,623,100 B2 * | 1/2014 | Fadli | ..................... | C07D 403/12 8/405 |
| 9,125,834 B2 * | 9/2015 | Couroux | .................. | A61Q 5/10 |
| 9,220,671 B2 * | 12/2015 | Ascione | ................ | A61K 8/492 |

FOREIGN PATENT DOCUMENTS

| | | | | |
|---|---|---|---|---|
| WO | 2014/003483 A1 * | 1/2014 | .......... | C07D 209/04 |
| WO | WO-2014003483 A1 | 1/2014 | | |
| WO | WO-2019074736 A1 | 4/2019 | | |

OTHER PUBLICATIONS

STIC Search Report Dated Sep. 8, 2020.*
"International Application Serial No. PCT/US2018/054106, International Search Report dated Dec. 19, 2018", 4 pgs.
"International Application Serial No. PCT/US2018/054106, Written Opinion dated Dec. 19, 2018", 7 pgs.

* cited by examiner

*Primary Examiner* — Eisa B Elhilo
(74) *Attorney, Agent, or Firm* — Victoria Friedman; Dennemeyer & Associates LLC

(57) ABSTRACT

A novel class of 3-halo-1H-indol-4-amine derivatives, particularly for dyeing keratin fibers, the azomethine dyes formed from them, their uses as a coupler for dyeing keratin fibers, hair dyeing compositions comprising them, method of dyeing hair thereof, and a hair dyeing kit thereof are disclosed. The products of the oxidative coupling with hair dye primary intermediates, particularly pyrazole derivative, a p-phenylenediamine derivative, a p-aminophenol derivative, have improved fastness properties over currently used violet-blue to blue azomethine dyes.

19 Claims, No Drawings

KERATIN DYEING COMPOUNDS, COMPOSITIONS CONTAINING THEM, AND METHOD AND USE THEREOF

PRIORITY

This application is a U.S. National Stage Filing under 35 U.S.C. 371 from International Application No. PCT/US2018/054106, filed on Oct. 3, 2018, and published as WO 2019/074736 on Apr. 18, 2019, which application claims the benefit of priority from U.S. Provisional Patent Application Ser. No. 62/572,020, filed on Oct. 13, 2017, which applications are herein incorporated in their entirety by reference.

TECHNICAL FIELD OF THE INVENTION

The present invention relates to a novel class of 3-halo-1H-indol-4-amine derivatives, particularly for dyeing keratin fibers, the azomethine dyes formed from them, their uses as a coupler for dyeing keratin fibers, hair dyeing compositions comprising them, method of dyeing hair thereof, and a hair dyeing kit thereof. The products of the oxidative coupling with hair dye primary intermediates, particularly pyrazole derivative, a p-phenylenediamine derivative, a p-aminophenol derivative, have improved fastness properties over currently used violet-blue to blue azomethine dyes.

BACKGROUND OF THE INVENTION

The permanent alteration of the color of fibers and substrates by dyes is well-known. In the case of keratinous fibers, in particular human hair, color modification by the application of hair dyes generally provides the consumer with the shade, longevity, and the intensity of color desired, when an oxidative coloring process involving complex chemical reactions is utilized. Permanent hair dyeing formulations typically comprise primary intermediates (also known as oxidative hair dye precursors or developers) and couplers (also known as color modifiers or secondary intermediates). These dye precursors are sufficiently small, polar and soluble to diffuse into the hair shaft where, once activated by an oxidizing agent (such as hydrogen peroxide) under basic conditions, the primary intermediates react with other dye precursors, e.g., couplers, to form larger, colored compounds in the hair shaft. The chromophores that are bigger, less polar and less soluble than the dye precursors that diffused into the fibers, do not readily diffuse out of the hair during subsequent washing with water and/or detergents.

A wide variety of developers and couplers have been employed in oxidative systems and compositions. However, one need that still remains is to provide a cool blue that is resistant to fading. Many current blue dyes wash out, leaving an unattractive brassy color to hair. In general, substitutions to either the coupler or developer that shift color into the blue region have a negative effect on the solubility, acid perspiration fastness, or shampoo fastness.

SUMMARY OF THE INVENTION

The present invention relates to novel compounds being 3-halo-1H-indol-4-amine derivatives, that provide azomethine dyes that give cool blue to green colors when reacted oxidatively with developers such as pyrazoles derivatives and p-phenylenediamines derivatives. These are useful as keratin dyeing compounds and overcome some of the performance limitations with previous azomethine dyes. This invention also relates to the use of these compounds being 3-halo-1H-indol-4-amine derivatives as a coupler for dyeing keratin fibers. This invention also relates to hair dyeing compositions comprising these compounds being 3-halo-1H-indol-4-amine derivatives as couplers, together with a suitable developer and an oxidizing agent. The invention also relates to a method for oxidatively dyeing of keratin fibers, comprising applying the hair dyeing compositions in the presence of an oxidizing agent, for a period sufficient to develop the desired coloration.

DETAILED DESCRIPTION OF THE INVENTION

While the specification concludes with claims which particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. When more than one composition is used during a treatment, as in mixing of the components of a typical oxidative dye product, the total weight to be considered is the total weight of all the compositions applied on the hair simultaneously (i.e. the weight found "on head") unless otherwise specified. The term "weight percent" may be denoted as "wt. %" herein.

As used herein, the term "hair" to be treated may be "living" i.e. on a living body or may be "non-living" i.e. in a wig, hairpiece or other aggregation of non-living keratinous fibers Mammalian, particularly human, hair is preferred. However, wool, fur, and other keratin containing fibers are suitable substrates for the compositions according to the present invention.

As used herein, the term "chromophore" means the part of the dye compound responsible for its color.

As used herein, the term "physiologically compatible salts" means salts that are suitable to be used with humans and have limited to no irritancy to humans.

As used herein, the term "substantially free" means that the hair dyeing compositions comprises less than 1%, preferably less than 0.1%, more preferably less than 0.01%, still more preferably is free of, a compound.

As used herein, the terms "developer" and "primary intermediary" are interchangeable.

As used herein, the term "compound" encompasses any tautomeric compound, if applicable, and except if stated otherwise. Hence, it is to be understood that when it is referred to a particular structure, all of the reasonable additional tautomeric structures are included. In the art, tautomeric structures are frequently represented by one single structure and the method described herein follows this general practice. For example, 2-mercaptopyridine (XX) may exist under known conditions in the pyridine-2-thione tautomer form (XXI).

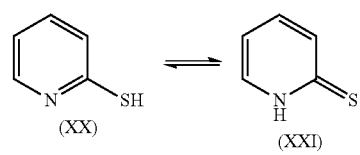

As used herein, the term "compound" encompasses any isomeric compound, if applicable, and except if stated otherwise. Hence, it is also understood that E, Z isomers may be involved, and that all of the reasonable additional E, Z isomers are included. For example, (E)-diphenyldiazene (XXII) converts under known conditions to (Z)-diphenyldiazene (XXIII), which is also reversible.

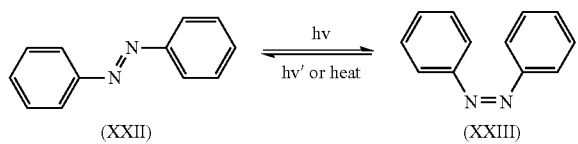

Novel 3-halo-1H-indol-4-amine Compounds

In a first aspect, the present invention relates to a novel 3-halo-1H-indol-4-amine compound of general formula (I)

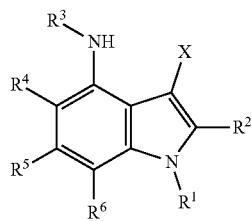

wherein radical X is an halogen atom selected from the group consisting of chlorine or bromine; wherein radicals $R^1$ and $R^3$ are the same or different and are selected from the group consisting of:
(a) N-linked monovalent substituents selected from the group consisting of:
  (i) substituted or unsubstituted, straight or branched, alkyl, mono- or poly-unsaturated alkyl, heteroalkyl, aliphatic, heteroaliphatic, or heteroolefinic systems;
  (ii) substituted or unsubstituted, mono- or poly-cyclic aliphatic;
  (iii) an aromatic ring or 5- or 6-membered heteroaromatic rings having at least one nitrogen, oxygen or sulfur atom; and,
  (iv) substituted or unsubstituted, mono- or polyhydroxy-, mono- or polyamino-, mono- or polyfluoroalkyl systems, or mixtures thereof; wherein said systems of (i) and (ii) comprise from about 1 to about 10 carbon atoms and from about 0 to about 5 heteroatoms selected from the group consisting of O, S, N, P, and Si;
(b) hydrogen;
(c) a linker group (L) between one of the radical $R^1$ or $R^3$ of a first compound of formula (I) and between one of the radical $R^1$ or $R^3$ of a second compound of formula (I), both compounds forming therefore a dimeric structure, wherein the linker group is of general formula (L)

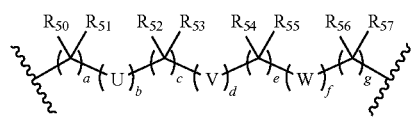

wherein
(i) a, c, e and g are each independently an integer from 0 to 3, provided that the sum of a, c, e and g is greater than or equal to 2; b, d and f are each independently 0 or 1; and $R_{50}$, $R_{51}$, $R_{52}$, $R_{53}$, $R_{54}$, $R_{55}$, $R_{56}$ and $R_{57}$ are each independently hydrogen or $C_1$-$C_2$ alkyl group;
(ii) U is an aromatic ring, alkenyl or alkynyl moiety;
(iii) V is O, N or S; and
(iv) W is a cyclic aliphatic ring;
wherein radicals $R^2$ and $R^5$ are the same or different and are selected from the group consisting of:
(a) C-linked monovalent substituents selected from the group consisting of:
  (i) substituted or unsubstituted, straight or branched, alkyl, mono- or poly-unsaturated alkyl, heteroalkyl, aliphatic, heteroaliphatic, or heteroolefinic systems;
  (ii) substituted or unsubstituted, mono- or poly-cyclic aliphatic;
  (iii) halogen atom;
  (iv) a boronic acid group, a boronic ester group;
  (v) an aromatic ring or 5- or 6-membered heteroaromatic rings having at least one nitrogen, oxygen or sulfur atom; and,
  (vi) substituted or unsubstituted, mono- or polyhydroxy-, mono- or polyamino-, mono- or polyfluoroalkyl systems, or mixtures thereof; wherein said systems of (i) and (ii) comprise from about 1 to about 10 carbon atoms and from about 0 to about 5 heteroatoms selected from the group consisting of O, S, N, P, and Si;
(b) S-linked monovalent substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;
(c) O-linked monovalent substituents selected from the group consisting of $OA^1$, and $ONA^1A^2$;
(d) N-linked monovalent substituents selected from the group consisting of $NA^1A^2$, $(NA^1A^2A^3)^+$, $NA^1OA^2$, $NA^1SA^2$, $N=NA^1$, $N=NOA^1$, $NA^1CN$, and $NA^1NA^2A^3$;
(e) monovalent substituents selected from the group consisting of $COOA^1$, $CONA^1_2$, $CONA^1COA^2$, and $C(=NA^1)NA^1A^2$;
(f) fluoroalkyl monovalent substituents selected from the group consisting of mono-, poly-, and per-fluoro alkyl systems comprising from about 1 to about 12 carbon atoms and from about 0 to about 4 heteroatoms; and
(g) hydrogen;
wherein $A^1$, $A^2$, and $A^3$ are monovalent and are independently selected from the group consisting of: H; substituted or unsubstituted, straight or branched, alkyl, mono- or poly-unsaturated alkyl, heteroalkyl, aliphatic, heteroaliphatic, or heteroolefinic systems; substituted or unsubstituted, mono- or poly-cyclic aliphatic, aryl, or heterocyclic systems; and substituted or unsubstituted, mono-, poly-, per-fluoro alkyl systems or $A^1$ and $A^2$ together with nitrogen atom to which they are bound form a ring;
wherein said systems comprise from about 1 to about 10 carbon atoms and from about 0 to about 5 heteroatoms selected from the group consisting of O, S, N, P, and Si;
wherein one of radicals $R^4$ or $R^6$ is selected from the group consisting of a hydrogen atom and/or a nucleofuge group;
wherein the other radical $R^6$ or $R^4$ is selected from the group consisting of:
(a) C-linked monovalent substituents selected from the group consisting of:

(i) substituted or unsubstituted, straight or branched, alkyl, mono- or poly-unsaturated alkyl, heteroalkyl, aliphatic, heteroaliphatic, or heteroolefinic systems;
(ii) substituted or unsubstituted, mono- or poly-cyclic aliphatic;
(iii) halogen atom;
(iv) a boronic acid group, a boronic ester group;
(v) an aromatic ring or 5- or 6-membered heteroaromatic rings having at least one nitrogen, oxygen or sulfur atom; and,
(vi) substituted or unsubstituted, mono- or polyhydroxy-, mono- or polyamino-, mono- or polyfluoroalkyl systems, or mixtures thereof; wherein said systems of (i) and (ii) comprise from about 1 to about 10 carbon atoms and from about 0 to about 5 heteroatoms selected from the group consisting of O, S, N, P, and Si;
(b) S-linked monovalent substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;
(c) O-linked monovalent substituents selected from the group consisting of $ONA^1A^2$;
(d) monovalent substituents selected from the group consisting of $COOA^1$, $CONA^1_2$, $CONA^1COA^2$, and $C(=NA^1)NA^1A^2$;
(e) fluoroalkyl monovalent substituents selected from the group consisting of mono-, poly-, and per-fluoro alkyl systems comprising from about 1 to about 12 carbon atoms and from about 0 to about 4 heteroatoms; and
(f) hydrogen;
wherein $A^1$, $A^2$, and $A^3$ are monovalent and are independently selected from the group consisting of: H; substituted or unsubstituted, straight or branched, alkyl, mono- or poly-unsaturated alkyl, heteroalkyl, aliphatic, heteroaliphatic, or heteroolefinic systems; substituted or unsubstituted, mono- or poly-cyclic aliphatic, aryl, or heterocyclic systems; and substituted or unsubstituted, mono-, poly-, per-fluoro alkyl systems or $A^1$ and $A^2$ together with nitrogen atom to which they are bound form a ring; wherein said systems comprise from about 1 to about 10 carbon atoms and from about 0 to about 5 heteroatoms selected from the group consisting of O, S, N, P, and Si; and,
their salts thereof;
wherein the 3-halo-1H-indol-4-amine compound of formula (1) is not the compound of formula (I.01) or of formula (I.02)

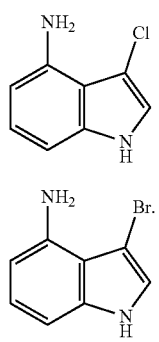

(I.01)

(I.02)

The inventors have found that the novel compounds of the present invention are particularly suitable for use as couplers for dyeing keratin fibers. Indeed, the inventors have found that these 3-halo-1H-indol-4-amines derivatives provide azomethine dyes that give cool blue to green colors when reacted oxidatively with developers. In addition, these 3-halo-1H-indol-4-amine derivatives allow overcoming some of the performance limitations with previous azomethine dyes, such as the inability to create colors that are pure blues from 4,5-diaminopyrazole compounds. Indeed, these 3-halo-1H-indol-4-amine derivatives provide improved fastness properties over currently used violet-blue to blue azomethine dyes.

The performance of the novel 3-halo-1H-indol-4-amine compounds of formula (I), when used as couplers for dyeing keratin fibers, may be assessed by measuring the CIE $L^*$, $a^*$, $b^*$, $C^*$, and $h^*$ values. For example, such values can be measured by using Minolta Spectrophotometer CM-3700d with D65 illumination. Data from the spectrophotometer provide coordinates for both $L^*a^*b^*$ and LCh color spaces. In both the $L^*a^*b^*$ and LCh color spaces, the $L^*$ value refers to lightness on a scale of zero to 100, with lower values indicating a darker color. In the $L^*a^*b^*$ color space, the coordinate $a^*$ designates a position between red and green, with higher numbers indicating a redder shade and lower numbers representing a greener shade. The coordinate $b^*$ designates a position between yellow and blue, with higher numbers indicating a yellower shade and lower numbers representing a bluer shade. In the LCh color space, the value C represents chroma, with higher values indicating a deeper, brighter color and lower values indicating a less deep, duller color. The value C in the LCh space is related to $a^*$ and $b^*$ in the $L^*a^*b^*$ space by the relationship $C=[(a^*)^2+(b^*)^2]^{1/2}$. The coordinate h in the LCh space represents hue angle, in which colors are represented as degree values from 0° to 360°.

When a salt of Formula (I) contains a cationic moiety, anionic counterions include, for example, D,L-malate, L-malate, D-malate, maleate, ascorbate, chloride, bromide, citrate, acetate, lactate, succinate, tartrate, phosphate, hemisulfate, sulfate, methylsulfate, trifluoroacetate, iodide, and mixtures thereof. When a salt of Formula (I) contains an anionic moiety, cationic counterions include, for example, ammonium, substituted ammonium salts (e.g., monoethanolammonium, diethanolammonium, triethanolammonium), sodium, potassium, and mixtures thereof.

The nucleofuge group may be selected from the group consisting of an alkoxy radical, an alkoxyalkyl radical, alkoxycarbonyl radical, an aryloxy group, a heteroaryloxy radical, an aryloxycarbonylamino radical, or an aryloxycarbonyl radical.

The aromatic ring or 5- or 6-membered heteroaromatic rings having at least one nitrogen oxygen or sulfur atom are, for any one of the radicals $R^1$, $R^2$, $R^3$, $R^4$, $R^5$ and/or $R^6$, may be selected from the group consisting pyridine, pyrrole, thiophene, furan, imidazole, thiazole, thiadiazole, pyrazole, oxazole, pyrimidine, naphthalene, benzothiazole, indole, benzoxazole, benzimidazole or azulene.

The halogen atom, for any one of the radicals $R^2$, $R^4$, $R^5$ and/or $R^6$, may be selected the group consisting of chlorine, bromine, iodine or fluorine.

Any one of the radicals $R^1$ and/or $R^3$ may be selected from the group consisting of a hydrogen atom, $C_1$-$C_6$ alkyl radical, $C_1$-$C_6$ hydroxyl alkyl radical, $C_1$-$C_6$ polyhydroxy alkyl radical, trifluoromethyl radical, aminoalkyl radical, polyaminoalkyl radical, N-substituted aminoalkyl radical, N,N-disubstituted aminoalkyl radical, acetylamido radical, a carboxyl radical, an alkoxy radical, an alkoxyalkyl radical, a carbamoyl radical, an alkylcarbamoylradical, a hydroxyalkylcarbamoyl radical, an amido radical, an alkylamido radical, an alkylcarbonyl radical, an alkoxycarbonyl radical, an aryloxy radical, an acyloxy radical, an alkylthio radical, an arylthio radical, a heteroarylthio radical, a heteroaryloxy radical, a 5- or 6-membered heterocycle having at least one nitrogen, oxygen or sulfur atom, which is optionally substituted, an aryl radical, which is optionally substituted, a sulfonyl radical, a sulfinyl radical, a phosphonyl radical, a sulfamoyl radical, a siloxy radical, an acyloxy radical, a carbamoyloxy radical, a sulphonamide radical, an imide radical, a ureido radical, a sulfamoylamino radical, an alkoxycarbonylamino radical, an aryloxycarbonylamino radical, an aryloxycarbonyl radical, and a benzenesulfonamido radical. Preferably, any one of the radicals $R^1$ and/or $R^3$ is selected from the group consisting of a hydrogen atom, a $C_1$-$C_6$ alkyl radical, a $C_1$-$C_6$ hydroxylalkyl radical, a $C_1$-$C_6$ polyhydroxy alkyl radical, a trifluoromethyl radical, an aminoalkyl radical, a polyaminoalkyl radical, N-substituted aminoalkyl radical, N,N-disubstituted radical, an aminohydroxyalkyl radical, an alkoxy radical, an alkoxyalkyl radical, an aryloxy radical, or a 5- or 6-membered heterocycle having at least one nitrogen, oxygen or sulfur atom. More preferably, any one of the radicals $R^1$ and/or $R^3$ is selected from the group consisting of a hydrogen atom, a $C_1$-$C_6$ alkyl radical, a $C_1$-$C_6$ hydroxyl alkyl radical, a $C_1$-$C_6$ polyhydroxy alkyl radical, an aminoalkyl radical, N-substituted aminoalkyl radical, N,N-disubstituted radical, aminohydroxyalkyl radical, or an alkoxyalkyl radical.

The radical $R^2$ may be selected from the group consisting of a hydrogen atom, a halogen atom, a $C_1$-$C_6$ alkyl radical, a $C_1$-$C_6$ hydroxyl alkyl radical, a $C_1$-$C_6$ polyhydroxy alkyl radical, a trifluoromethyl radical, an alkylamino radical, a hydroxyalkylamino radical, an acetylamido radical, a carboxyl radical, an alkoxy radical, an alkoxyalkyl radical, a carbamoyl radical, an alkylcarbamoylradical, a hydroxylkylcarbamoyl radical, an amido radical, an alkylamido radical, an alkylcarbonyl radical, an alkoxycarbonyl radical, an aryloxy radical, an acyloxy radical, an alkylthio radical, an arylthio radical, a heteroarylthio radical, a heteroaryloxy radical, a 5- or 6-membered heterocycle having at least one nitrogen, oxygen or sulfur atom, which is optionally substituted, an aryl radical, which is optionally substituted, a sulfonyl radical, a sulfinyl radical, a phosphonyl radical, a sulfamoyl radical, a siloxy radical, an acyloxy radical, a carbamoyloxy radical, a sulphonamide radical, an imide radical, an ureido radical, a sulfamoylamino radical, an alkoxycarbonylamino radical, an aryloxycarbonylamino radical, an aryloxycarbonyl radical, and a benzenesulfonamido radical. Preferably, the radical $R^2$ is selected from the group consisting of a hydrogen atom, a halogen atom, a $C_1$-$C_6$ alkyl radical, a $C_1$-$C_6$ hydroxyl alkyl radical, a $C_1$-$C_6$ polyhydroxy alkyl radical, a trifluoromethyl radical, an alkylamino radical, a hydroxyalkylamino radical, an acetylamido radical, a carboxyl radical, an alkoxy radical, an alkoxyalkyl radical, a carbamoyl radical, an alkylcarbamoylradical, a hydroxylkylcarbamoyl radical, an amido radical, an alkylamido radical, an alkylcarbonyl radical, an alkoxycarbonyl radical, an aryloxy radical, or an acyloxy radical. More preferably, the radical $R^2$ is selected from the group consisting of a hydrogen atom, a halogen atom, a $C_1$-$C_6$ alkyl radical, a $C_1$-$C_6$ hydroxyl alkyl radical, a $C_1$-$C_6$ polyhydroxy alkyl radical, a trifluoromethyl radical, an alkylamino radical, a hydroxyalkylamino radical, an alkoxy radical, an alkoxyalkyl radical, or an aryloxy radical. Still more preferably, the radical $R^2$ is selected from the group consisting of a hydrogen atom, or a $C_1$-$C_6$ alkyl radical. Most preferably, the radical $R^2$ is a hydrogen atom.

The radical $R^5$ may selected from the group consisting of a hydrogen atom, a halogen atom, an amino radical, a hydroxyl radical, a $C_1$-$C_6$ alkyl radical, a $C_1$-$C_6$ hydroxyl alkyl radical, a $C_1$-$C_6$ polyhydroxy alkyl radical, a trifluoromethyl radical, an alkylamino radical, a hydroxyalkylamino radical, an acetylamido radical, a carboxyl radical, an alkoxy radical, an alkoxyalkyl radical, a carbamoyl radical, an alkylcarbamoylradical, a hydroxyalkylcarbamoyl radical, an amido radical, an alkylamido radical, an alkylcarbonyl radical, an alkoxycarbonyl radical, an aryloxy radical, an acyloxy radical, an alkylthio radical, an arylthio radical, a heteroarylthio radical, a heteroaryloxy radical, a 5- or 6-membered heterocycle having at least one nitrogen, oxygen or sulfur atom, which is optionally substituted, an aryl radical, which is optionally substituted, a sulfonyl radical, a sulfinyl radical, a phosphonyl radical, a sulfamoyl radical, a siloxy radical, an acyloxy radical, a carbamoyloxy radical, a sulphonamide radical, an imide radical, an ureido radical, a sulfamoylamino radical, an alkoxycarbonylamino radical, an aryloxycarbonylamino radical, an aryloxycarbonyl radical, and a benzenesulfonamido radical. Preferably, the radical $R^5$ is selected from the group consisting of a hydrogen atom, a halogen atom, an amino radical, a hydroxyl radical, a $C_1$-$C_6$ alkyl radical, a $C_1$-$C_6$ hydroxyl alkyl radical, a $C_1$-$C_6$ polyhydroxy alkyl radical, a trifluoromethyl radical, an alkylamino radical, a hydroxyalkylamino radical, an acetylamido radical, a carboxyl radical, an alkoxy radical, an alkoxyalkyl radical, a carbamoyl radical, an alkylcarbamoylradical, a hydroxyalkylcarbamoyl radical, an amido radical, an alkylamido radical, an alkylcarbonyl radical, an alkoxycarbonyl radical, an aryloxy radical, or an acyloxy radical. More preferably, the radical $R^5$ is selected from the group consisting of a hydrogen atom, a halogen atom, an amino radical, a hydroxyl radical, a $C_1$-$C_6$ alkyl radical, a $C_1$-$C_6$ hydroxyl alkyl radical, a $C_1$-$C_6$ polyhydroxy alkyl radical, a trifluoromethyl radical, an alkylamino radical, a hydroxyalkylamino radical, an alkoxy radical, an alkoxyalkyl radical, or an aryloxy radical. Still more preferably, the radical $R^5$ is selected from the group consisting of a hydrogen atom, or a $C_1$-$C_6$ alkyl radical. Most preferably, the radical $R^5$ is a hydrogen atom.

The other radical $R^6$ or $R^4$ may be selected from the group consisting of a hydrogen atom, a halogen atom, a $C_1$-$C_6$ alkyl radical, a $C_1$-$C_6$ hydroxyl alkyl radical, a $C_1$-$C_6$ polyhydroxy alkyl radical, a trifluoromethyl radical, a carboxyl radical, an alkoxy radical, an alkoxyalkyl radical, a carbamoyl radical, an alkylcarbamoylradical, a hydroxyalkylcarbamoyl radical, an alkylcarbonyl radical, an alkoxycarbonyl radical, an aryloxy radical, an acyloxy radical, an alkylthio radical, an arylthio radical, a heteroarylthio radical, a heteroaryloxy radical, a 5- or 6-membered heterocycle having at least one nitrogen, oxygen or sulfur atom, which is optionally substituted, an aryl radical, which is optionally substituted, a sulfonyl radical, a sulfinyl radical, a phosphonyl radical, a sulfamoyl radical, a siloxy radical, an acyloxy radical, a carbamoyloxy radical, a sulphonamide radical, an imide radical, an ureido radical, a sulfamoylamino radical, an alkoxycarbonylamino radical, an aryloxycarbonylamino radical, an aryloxycarbonyl radical, and a benzenesulfonamido radical. Preferably, the other radical $R^6$ or $R^4$ is selected from the group consisting of a hydrogen atom, a halogen atom, a $C_1$-$C_6$ alkyl radical, a $C_1$-$C_6$ hydroxyl alkyl radical, a $C_1$-$C_6$ polyhydroxy alkyl radical, a trifluoromethyl radical, a carboxyl radical, an alkoxy radical, an alkoxyalkyl radical, a carbamoyl radical, an alkylcarbamoylradical, a hydroxyalkylcarbamoyl radical, an alkylcarbonyl radical, an alkoxycarbonyl radical, an aryloxy radical, or an acyloxy radical. More preferably, the other radical $R^6$ or $R^4$ is selected from the group consisting of a hydrogen atom, a halogen atom, a $C_1$-$C_6$ alkyl radical, a $C_1$-$C_6$ hydroxyl alkyl radical, a $C_1$-$C_6$ polyhydroxy alkyl radical, a trifluoromethyl radical, an alkoxy radical, an alkoxyalkyl radical, or an aryloxy radical. Still more preferably, the other radical $R^6$ or $R^4$ is selected from the group consisting of a hydrogen atom, or a $C_1$-$C_6$ alkyl radical. Most preferably, the other radical $R^6$ or $R^4$ is a hydrogen atom.

In one embodiment, radicals $R^6$ and $R^4$ are hydrogen.

The compound may be selected from the group consisting of

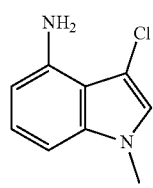
(I.03)

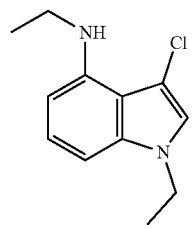
(I.04)

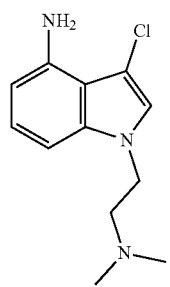
(I.05)

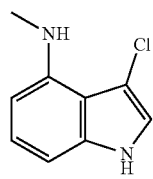
(I.06)

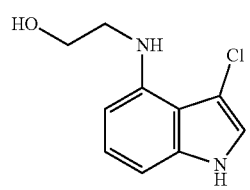
(I.07)

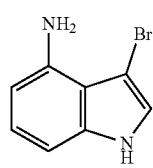
(I.08)

-continued

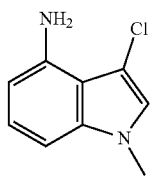
(I.09)

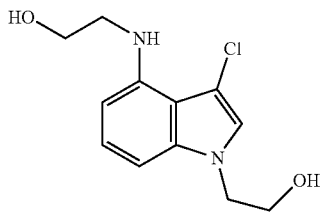
(I.10)

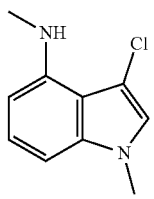
(I.11)

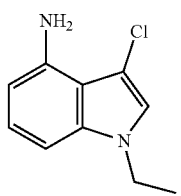
(I.12)

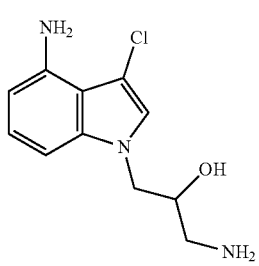
(I.13)

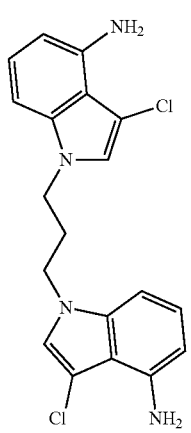
(I.14)

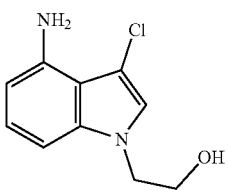
(I.15)

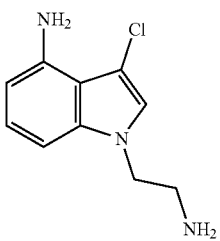
(I.16)

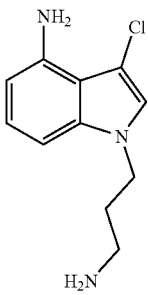
(I.17)

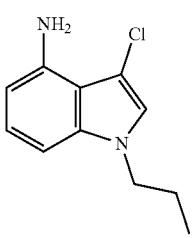
(I.18)

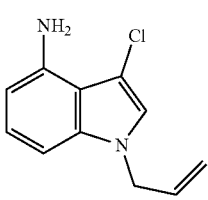
(I.19)

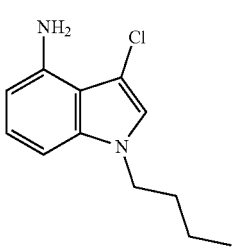
(I.20)

(I.21)

(I.22)

(I.23)

As used herein, the alkylamino radical may be selected from the group of radicals consisting of: N,N-dimethylamino, N,N-diethylamino, N-methylamino, or N-ethylamino. The hydroxyalkylamino radical may be selected from the group of radicals consisting of: N-(hydroxyethyl)amino, N-hydroxymethylamino, N-hydroxypropylamino, N,N-bis(hydroxyethyl)amino, N-(2,3-dihydroxypropyl)amino or N,N-bis(hydroxypropyl)amino). The alkoxy radical may be selected from the group of radicals consisting of: methoxy, ethoxy, propyloxy, benzyloxy, methoxyethoxy, phenoxyethoxy, 2-cyanoethoxy, phenethyloxy, phenoxyethoxy, p-chlorobenzyloxy or methoxyethylcarbamoylmethoxy; preferably from methoxy, ethoxy, propyloxy, benzyloxy, methoxyethoxy, or phenoxyethoxy. The alkoxyalkyl radical may be selected from the group of radicals consisting of: methoxymethyl, methoxyethyl, methoxypropyl, ethoxymethyl, ethoxyethyl or ethoxypropyl. The alkylcarbamoylradical may be selected from the group of radicals consisting of: methylcarbamoyl, ethylcarbamoyl, dimethylcarbamoyl, or diethylcarbamoyl. The hydroxyalkylcarbamoyl radical may be selected from the group of radicals consisting of: 2-hydroxyethylcarbamoyl, bis(2-hydroxyethyl)carbamoyl, hydroxymethylcarbamoyl, bis(hydroxymethyl)carbamoyl). The alkylamido radical may be selected from the group of radicals consisting of: acetamido, propionamido, or butyramido. The alkylcarbonyl radical may be selected from the group of radicals consisting of: acetyl, butyryl, or propionyl. The alkoxycarbonyl radical may be selected from the group of radicals consisting of: methoxycarbonyl, ethoxycarbonyl, or propoxycarbonyl. The aryloxy radical may be selected from the group of radicals consisting of: phenoxy, 4-methoxyphenoxy, 4-nitrophenoxy, 4-cyanophenoxy, 4-methanesulfonamidophenoxy, 4-methanesulfonylphenoxy, 3-methylphenoxy or 1-naphthyloxy; preferably from phenoxy, 4-methoxyphenoxy, or 4-nitrophenoxy. The acyloxy radical may be selected from the group of radicals consisting of: acetoxy, propanoyloxy, benzolyloxy, 2,4-dichlorobenzolyloxy, ethoxyalkyloxy, pyruviloyloxy, cinnamoyloxy or myristoyloxy. The alkylthio radical may be selected from the group of radicals consisting of: methylthio, ethylthio, propylthio, butylthio, 2-cyanoethylthio, benzylthio, phenethylthio, 2-(diethylamino)ethylthio, ethoxyethylthio or phenoxyethylthio. The arylthio radical may be selected from the group of radicals consisting of: phenylthio, 4-carboxyphenylthio, 2-ethoxy-5-tert-butylphenylthio, 2-carboxyphenylthio or 4-methanesulfonylphenylthio. The heteroarylthio radical may be selected from the group of radicals consisting of: 5-phenyl-2,3,4,5-tetrazolyloxy or 2-benzothiazolyloxy. The heteroaryloxy radical may be selected from the group of radicals consisting of: 5-phenyl-2,3,4,5-tetrazolyloxy or 2-benzothiazolyloxy. The 5- or 6-membered heterocycle having at least one nitrogen, oxygen or sulfur atom may be selected from the group of radicals consisting of: pyridyl, quinolyl, morpholyl, furyl, tetrahydrofuryl, pyrazolyl, triazolyl, tetrazolyl, triazolyl, oxazolyl, imidazolyl or thiadiazolyl, and is optionally substituted. The aryl radical may be selected from the group of radicals consisting of: phenyl or naphthyl, and is optionally substituted.

Novel 3-halo-1H-indol-4-amine Compounds as Couplers for Dyeing Keratin Fibers

In a second aspect, the present invention relates to the use of a 3-halo-1H-indol-4-amine compound, as a coupler for dyeing keratin fibers; preferably human keratin fibers; more preferably human hair;

wherein the 3-halo-1H-indol-4-amine compound is a compound of general formula (I)

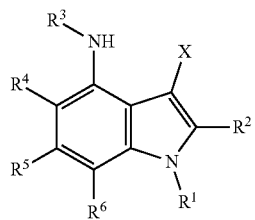

(I)

wherein radical X is an halogen atom selected from the group consisting of chlorine or bromine; wherein radicals $R^1$ and $R^3$ are the same or different and are selected from the group consisting of:
(a) N-linked monovalent substituents selected from the group consisting of:
  (i) substituted or unsubstituted, straight or branched, alkyl, mono- or poly-unsaturated alkyl, heteroalkyl, aliphatic, heteroaliphatic, or heteroolefinic systems;
  (ii) substituted or unsubstituted, mono- or poly-cyclic aliphatic;
  (iii) an aromatic ring or 5- or 6-membered heteroaromatic rings having at least one nitrogen, oxygen or sulfur atom; and,
  (iv) substituted or unsubstituted, mono- or polyhydroxy-, mono- or polyamino-, mono- or polyfluoroalkyl systems, or mixtures thereof; wherein said systems of (i) and (ii) comprise from about 1 to about 10 carbon atoms and from about 0 to about 5 heteroatoms selected from the group consisting of O, S, N, P, and Si;
(b) hydrogen;
(c) a linker group (L) between one of the radical $R^1$ or $R^3$ of a first compound of formula (I) and between one of the radical $R^1$ or $R^3$ of a second compound of formula (I), both compounds forming therefore a dimeric structure, wherein the linker group is of general formula (L) wherein

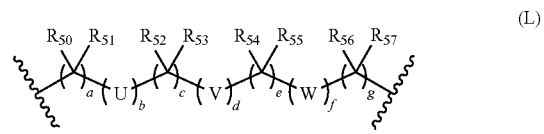

(L)

(i) a, c, e and g are each independently an integer from 0 to 3, provided that the sum of a, c, e and g is greater than or equal to 2; b, d and f are each independently 0 or 1; and $R^{50}$, $R^{51}$, $R^{52}$, $R^{53}$, $R^{54}$, $R^{55}$, $R^{56}$ and $R^{57}$ are each independently hydrogen or $C_1$-$C_2$ alkyl group;
  (ii) U is an aromatic ring, alkenyl or alkynyl moiety;
  (iii) V is O, N or S; and
  (iv) W is a cyclic aliphatic ring;

wherein radicals $R^2$ and $R^5$ are the same or different and are selected from the group consisting of:
(a) C-linked monovalent substituents selected from the group consisting of:
  (i) substituted or unsubstituted, straight or branched, alkyl, mono- or poly-unsaturated alkyl, heteroalkyl, aliphatic, heteroaliphatic, or heteroolefinic systems;
  (ii) substituted or unsubstituted, mono- or poly-cyclic aliphatic;
  (iii) halogen atom;
  (iv) a boronic acid group, a boronic ester group;
  (v) an aromatic ring or 5- or 6-membered heteroaromatic rings having at least one nitrogen, oxygen or sulfur atom; and,
  (vi) substituted or unsubstituted, mono- or polyhydroxy-, mono- or polyamino-, mono- or polyfluoroalkyl systems, or mixtures thereof; wherein said systems of (i) and (ii) comprise from about 1 to about 10 carbon atoms and from about 0 to about 5 heteroatoms selected from the group consisting of O, S, N, P, and Si;
(b) S-linked monovalent substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;
(c) O-linked monovalent substituents selected from the group consisting of $OA^1$, and $ONA^1A^2$;
(d) N-linked monovalent substituents selected from the group consisting of $NA^1A^2$, $(NA^1A^2A^3)^+$, $NA^1OA^2$, $NA^1SA^2$, $N=NA^1$, $N=NOA^1$, $NA^1CN$, and $NA^1NA^2A^3$;
(e) monovalent substituents selected from the group consisting of $COOA^1$, $CONA^1_2$, $CONA^1COA^2$, and $C(=NA^1)NA^1A^2$;
(f) fluoroalkyl monovalent substituents selected from the group consisting of mono-, poly-, and per-fluoro alkyl systems comprising from about 1 to about 12 carbon atoms and from about 0 to about 4 heteroatoms; and
(g) hydrogen;
wherein $A^1$, $A^2$, and $A^3$ are monovalent and are independently selected from the group consisting of: H; substituted or unsubstituted, straight or branched, alkyl, mono- or poly-unsaturated alkyl, heteroalkyl, aliphatic, heteroaliphatic, or heteroolefinic systems; substituted or unsubstituted, mono- or poly-cyclic aliphatic, aryl, or heterocyclic systems; and substituted or unsubstituted, mono-, poly-, per-fluoro alkyl systems or $A^1$ and $A^2$ together with nitrogen atom to which they are bound form a ring; wherein said systems comprise from about 1 to about 10 carbon atoms and from about 0 to about 5 heteroatoms selected from the group consisting of O, S, N, P, and Si;

wherein one of radicals $R^4$ or $R^6$ is selected from the group consisting of a hydrogen atom and/or a nucleofuge group;

wherein the other radical $R^6$ or $R^4$ or is selected from the group consisting of:

(a) C-linked monovalent substituents selected from the group consisting of:
   (i) substituted or unsubstituted, straight or branched, alkyl, mono- or poly-unsaturated alkyl, heteroalkyl, aliphatic, heteroaliphatic, or heteroolefinic systems;
   (ii) substituted or unsubstituted, mono- or poly-cyclic aliphatic;
   (iii) halogen atom;
   (iv) a boronic acid group, a boronic ester group;
   (v) an aromatic ring or 5- or 6-membered heteroaromatic rings having at least one nitrogen, oxygen or sulfur atom; and,
   (vi) substituted or unsubstituted, mono- or polyhydroxy-, mono- or polyamino-, mono- or polyfluoroalkyl systems, or mixtures thereof; wherein said systems of (i) and (ii) comprise from about 1 to about 10 carbon atoms and from about 0 to about 5 heteroatoms selected from the group consisting of O, S, N, P, and Si;

(b) S-linked monovalent substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;

(c) O-linked monovalent substituents selected from the group consisting of $ONA^1A^2$;

(d) monovalent substituents selected from the group consisting of $COOA^1$, $CONA^1{}_2$, $CONA^1COA^2$, $C(=NA^1)NA^1A^2$, and CN;

(e) fluoroalkyl monovalent substituents selected from the group consisting of mono-, poly-, and per-fluoro alkyl systems comprising from about 1 to about 12 carbon atoms and from about 0 to about 4 heteroatoms; and (f) hydrogen;

wherein $A^1$, $A^2$, and $A^3$ are monovalent and are independently selected from the group consisting of: H; substituted or unsubstituted, straight or branched, alkyl, mono- or poly-unsaturated alkyl, heteroalkyl, aliphatic, heteroaliphatic, or heteroolefinic systems; substituted or unsubstituted, mono- or poly-cyclic aliphatic, aryl, or heterocyclic systems; and substituted or unsubstituted, mono-, poly-, per-fluoro alkyl systems or $A^1$ and $A^2$ together with nitrogen atom to which they are bound form a ring; wherein said systems comprise from about 1 to about 10 carbon atoms and from about 0 to about 5 heteroatoms selected from the group consisting of O, S, N, P, and Si;

and their salts thereof.

Hair Dyeing Compositions

In a third aspect, the present invention relates to a hair dyeing composition comprising:

(a) a coupler being a 4-amino-indole compound of formula (I), as described hereinbefore;
(b) a developer; and
(c) an oxidizing agent.

The hair dyeing composition may comprise from 0.005% to 5%; preferably from 0.01% to 4%; more preferably from 0.1 to 3.5% of a coupler being a 4-amino-indole compound of formula (I), by weight of the total composition.

The hair dyeing composition may comprise from 0.005% to 5%; preferably from 0.01% to 4%; more preferably from 0.1 to 3.5%; of a developer, by weight of the total composition.

The hair dyeing composition may comprise from 0.1% to 3%; preferably from 0.5% to 4.5%; more preferably from 1% to 8%; of an oxidizing agent, by weight of the total composition.

Couplers

A suitable coupler is the 4-amino-indole compound of formula (I), as described hereinbefore.

Developers

The developer may be selected from the group consisting of a pyrazole derivative, a p-phenylenediamine derivative, a p-aminophanol derivatives, their physiologically compatible water-soluble salts, or combinations thereof.

The pyrazole derivative may be a compound of general formula (V)

(V)

wherein radical $R^7$ is selected from the group consisting of hydrogen, a saturated $(C_1\text{-}C_6)$-alkyl group, an unsaturated $(C_2\text{-}C_6)$-alkyl group, a $(C_2\text{-}C_6)$-hydroxyalkyl group, a $(C_3\text{-}C_6)$-polyhydroxyalkyl group, a $(C_1\text{-}C_6)$-alkoxy-$(C_2\text{-}C_6)$-alkyl group, a substituted or unsubstituted benzyl group, a substituted or unsubstituted phenyl group, a substituted or unsubstituted 5- or 6-membered heteroaryl group, a substituted or unsubstituted thiazolylmethyl group, a quaternary group $Q^+$ linked to the pyrazole ring via a $(C_1\text{-}C_2)$-alkylene diradical or a phenylene diradical, wherein $Q^+$ represents (a) a quaternary trialkylammonium, wherein the alkyl-groups may be identical or different and, independently of one another, are a saturated or unsaturated $(C_1\text{-}C_{12})$-alkyl group; or (b) an aromatic substituted or unsubstituted 4- to 6-membered heterocyclic quaternary ammonium group, which may contain other heteroatoms like nitrogen, sulfur or oxygen, with the proviso that the cationic heterocycle comprises at most three heteroatoms, where the heterocycle has at most one sulfur atom or oxygen atom and the benzocondensed form of these 4- to 6-membered heterocyclic quaternary ammonium group;

or group between the radical $R^7$ of a first compound of formula (V) and between the radical $R^7$ of a second compound of formula (V), both compounds forming therefore a dimeric structure, wherein the linker group is of general formula (VI);

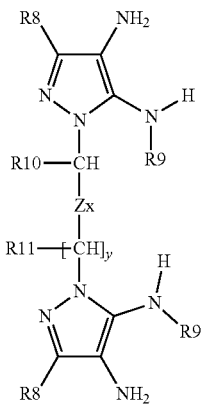

(VI)

wherein radical $R^8$ is selected from the group consisting of hydrogen, a saturated ($C_1$-$C_6$)-alkyl group, an unsaturated ($C_2$-$C_6$)-alkyl group, a ($C_2$-$C_6$)-hydroxyalkyl group, a ($C_2$-$C_6$)-aminoalkyl group, a ($C_1$-$C_4$)-alkylamino-($C_1$-$C_4$)-alkyl group, a di($C_1$-$C_4$)-alkylamino-($C_1$-$C_4$)-alkyl group, a substituted or unsubstituted benzyl group, a $C_1$-$C_6$ alkoxyl group, a substituted or unsubstituted phenoxyl or aryloxyl group, a substituted or unsubstituted aryl or heteroaryl group, a carboxylic acid group, a carboxylic acid ester group, a carboxamide group, a nitrile group, or $R^8$ of a first compound is linked with R;

wherein radical $R^9$ is selected from the group consisting of hydrogen, a saturated ($C_1$-$C_6$)-alkyl group, an unsaturated ($C_2$-$C_6$)-alkyl group, a ($C_2$-$C_6$)-hydroxyalkyl group, a ($C_3$-$C_6$)-dihydroxyalkyl group, a ($C_1$-$C_4$)-alkoxy-($C_1$-$C_4$)-alkyl group or a benzyl group; radicals $R^{10}$ and $R^{11}$, independently of each other, are the same or different and each represent hydrogen, a saturated ($C_1$-$C_6$)-alkyl group, an unsaturated ($C_2$-$C_6$)-alkyl group, a ($C_2$-$C_6$)-hydroxyalkyl group, an hydroxy group, an aryl group, an heteroaryl group, a carboxylic acid group, a carboxylic ester group, a substituted or unsubstituted carboxylic amide group, or $R^{10}$ and $R^{11}$ together represent an unsubstituted or substituted ($C_1$-$C_6$)-alkylene group;

wherein radical Z represents a ($C_1$-$C_{10}$)-alkyl diradical, which is optionally interrupted by an heteroatom, for example a nitrogen, an oxygen or a sulfur atom, an aromatic or heteroaromatic diradical, which may be substituted optionally with a hydroxyl group or a ($C_1$-$C_6$)-alkyl group and/or may be subjected to a benzocondensation once or twice; or a diradical of formula —Ar(Alk)$_n$-Ar—, wherein Ar represents an arylene group or a heteroarylene group (especially a phenylene group or pyridylene group), which may optionally be substituted, Alk represents a —CH$_2$— group and n represents a number from 0 to 6; and x and y independently of each other represents 0 or 1.

The pyrazole derivative may be selected from the group consisting of 1-methyl-1H-pyrazole-4,5-diamine, 2-(4,5-diamino-1H-pyrazol-1-yl)ethanol, 1-isopropyl-1H-pyrazole-4,5-diamine, 1-(4-methylbenzyl)-1H-pyrazole-4,5-diamine, 1-(benzyl)-1H-pyrazole-4,5-diamine, 1-(4-chlorobenzyl)-1H-pyrazole-4,5-diamine, 1-(heptyl)-1H-pyrazole-4,5-diamine, 1-(pentyl)-1H-pyrazole-4,5-diamine, 1-(hexyl)-1H-pyrazole-4,5-diamine, their physiologically acceptable salts thereof, or mixtures thereof; preferably 2-(4,5-diamino-1H-pyrazol-1-yl)ethanol and 1-(hexyl)-1H-pyrazole-4,5-diamine, their physiologically acceptable salts thereof, or mixtures thereof.

The p-phenylenediamine derivative may be a compound of general formula (VII)

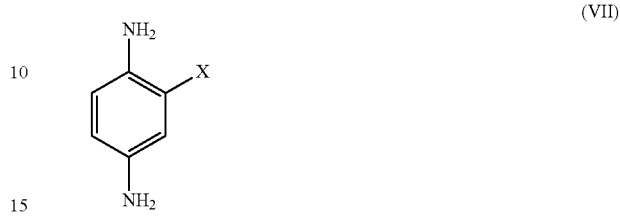

(VII)

wherein radical X is selected from the group consisting of:
(a) a hydrogen,
(b) a $C_1$-$C_6$ alkyl, preferably methyl, ethyl, propyl, butyl;
(c) methoxy, ethoxy, propoxy, isopropoxy or butoxy;
(d) $C_1$-$C_6$ alkyl with hydroxy substitution;
(e) —(CH$_2$)$_y$—O—CH$_3$; y being from 1-3;
(f) —(CH$_2$)$_y$—O—CH$_2$CH$_3$; y being from 1-3;
(g) —(CH$_2$)$_y$—O—CH$_2$CH$_2$CH$_3$; y being from 1-3;
(h)

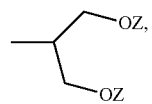

Z being hydrogen or $C_{1-3}$ alkyl;
and mixtures thereof.

The p-aminophenol derivative may be a compound of formula (VIII)

(VIII)

wherein radical X is selected from the group consisting of:
(a) a hydrogen
(b) a $C_1$-$C_6$ alkyl radical; preferably methyl, ethyl, propyl, butyl;
(c) methoxy, ethoxy, propoxy, isopropoxy or butoxy;
(d) $C_1$-$C_6$ alkyl radical with hydroxy substitution;
(e) —(CH$_2$)$_y$—O—CH$_3$; y is from 1-3;
(f) —(CH$_2$)$_y$—O—CH$_2$CH$_3$; y is from 1-3;
(g) —(CH$_2$)$_y$—O—CH$_2$CH$_2$CH$_3$; y is from 1-3;
(h)

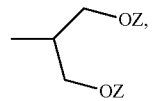

Z is hydrogen or $C_{1-3}$ alkyl radical;
and mixtures thereof;
wherein the substitutions of the X moiety can be on the 2 or the 3 position of the benzene ring.

The developer may also be one of the following compounds:

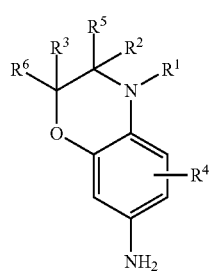

(IX)

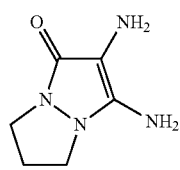

(X)

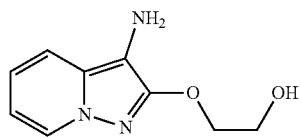

(XI)

Oxidizing Agent

The hair dyeing composition described herein also comprise at least one source of an oxidizing agent. Preferred oxidizing agents for use herein are water soluble peroxygen oxidizing agents. Water-soluble peroxygen oxidizing agents are well known in the art and include, but are not limited to, hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulfates and the like. These inorganic perhydrate salts may be incorporated as monohydrates, tetrahydrates etc. Alkyl and aryl peroxides, and or peroxidases, oxidases, and uricases and their substrates may also be used. Mixtures of two or more such oxidizing agents can also be used if desired. The oxidizing agents may be provided in aqueous solution or as a powder which is dissolved prior to use. In an embodiment, the oxidizing agents may be selected from the group consisting of hydrogen peroxide, percarbonate, persulfates and combinations thereof.

In an embodiment, the hair dyeing composition may comprise from about 0.1% to about 20% by weight, or from about 1% to about 15% by weight, or from about 2% to about 10% by weight of the oxidizing agent.

A potential oxidizing agent for use herein is a source of peroxymonocarbonate ions formed in situ from a source of hydrogen peroxide and a hydrogen carbonate ion source. Moreover, this system is also particularly effective in combination with a source of ammonia or ammonium ions. Accordingly, any source of these peroxymonocarbonate ions may be used. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may be used both as an oxidizing agent and as a source of carbonate ions. Preferred sources of carbonate ions, carbamate and hydrocarbonate ions are sodium hydrogen carbonate, potassium hydrogen carbonate, ammonium carbamate, and mixtures thereof.

The oxidizing agent may comprise from 0.1% to 15% by weight, or from 1% to 10% by weight, or from 1% to 8% by weight of a hydrogen carbonate ion; and from 0.1% to 10% by weight, or from 1% to 7% by weight, or from 2% to 5% by weight of the oxidizing agent of a source of hydrogen peroxide.

Optional Ingredients

In addition to the new couplers that provide cool, long-lasting blue colors, developers, and oxidizing agents, the hair dyeing compositions of the present invention may include optional additional compounds. Suitable optional ingredients include, but are not limited to: solvents; oxidizing agents; alkalizing agents; additional oxidative dye precursors, direct dyes; chelants; radical scavengers; pH modifiers and buffering agents; thickeners and/or rheology modifiers; carbonate ion sources; peroxymonocarbonate ion sources; anionic, cationic, nonionic, amphoteric or zwitterionic surfactants, and mixtures thereof; anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Solvents

The hair dyeing compositions described herein may further comprise a solvent. The solvent may be selected from water, or a mixture of water and at least one organic solvent to dissolve the compounds that would not typically be sufficiently soluble in water.

Suitable organic solvents include, but are not limited to: $C_1$ to $C_4$ lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

In an embodiment, the solvent may be selected from the group consisting of water, ethanol, propanol, isopropanol, glycerol, 1,2-propylene glycol, hexylene glycol, ethoxy diglycol, and mixtures thereof.

The composition may comprise water as a main ingredient, particularly in a total amount ranging from at least about 20%, alternatively from at least about 40%, alternatively from at least about 70%, by weight of the total composition. In an embodiment, the composition may comprise a total amount of organic solvents ranging from about 1% to about 30%, by weight of the total hair dyeing composition.

Alkalizing Agent

The hair dyeing composition described herein may further comprise an alkalizing agent as known in the art. Any alkalizing agent known in the art may be used such as ammonia, alkanolamines for example monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol, guanidium salts, alkali metal and ammonium hydroxides such as sodium hydroxide, alkali metal and ammonium carbonates, and mixtures thereof. In an embodiment, the alkalizing agent may be ammonia and/or monoethanolamine.

The hair dyeing compositions described herein may comprise from about 0.1% to about 10%, preferably from about 0.5% to about 6%, more preferably from about 1% to about 4% by weight of the alkalizing agent relative to the total weight of the composition.

The hair dyeing compositions described above may have a pH of from 7 to 12, alternatively from 8 to 11. For embodiments comprising a peroxymonocarbonate ion, the pH may be up to and including pH 9.5, alternatively from 7.5 to 9.5, alternatively from 8.4 to 9.5, alternatively from 8.5 to 9.4, alternatively 9.0, and alternatively 9.3.

Any sub-components of the hair dyeing compositions, such as a tint composition or an oxidizing composition, may have a different pH from the hair dyeing composition. For example, if the tint composition comprises an alkalizing agent, the tint composition will have an alkaline pH, such as higher than 7. In an embodiment, the oxidizing composition may comprise an acidic pH of less than 7.

When the hair dyeing composition described herein is obtained by mixing a developer and a tint composition prior to use, the alkalizing agent is generally present in the tint composition.

Additional Oxidative Dye Precursors

In addition to the direct dye compounds described herein, the hair dyeing composition may further comprise one or more oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

In an embodiment, the hair dyeing composition may comprise a total amount of oxidative dye precursors ranging up to about 12%, alternatively from about 0.1% to about 10%, alternatively from about 0.3% to about 8%, alternatively from about 0.5% to about 6%, by weight of the total composition.

Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino) ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, (2,3-diamino-6,7-dihydro-1H,5H-pyrazolo [1,2-a]pyrazol-1-one dimethanesulfonate), 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy]ethanol hydrochloride, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl) aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

When the hair dyeing composition described herein is obtained by mixing a tint composition and a developer composition, the primary intermediates and couplers may be incorporated into the tint composition.

Alternatively, the hair dyeing composition may be substantially free of any additional oxidative dye precursors.

Additional Direct Dyes

The hair dyeing composition may further comprise additional compatible direct dyes, in an amount sufficient to provide additional coloring, particularly with regard to intensity. In an embodiment, the composition may comprise a total amount of direct dyes ranging from about 0.05% to about 4%, by weight of the total composition.

Suitable direct dyes include but are not limited to: HC Yellow 17, HC Blue 18, HC Yellow 16, HC Red 18, Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl) (ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)bu-tane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

When the hair dyeing composition is obtained by mixing a tint composition and a developer composition, the additional direct dyes may be incorporated into the tint composition.

Alternatively, the hair dyeing composition may be substantially free of any additional direct dyes.

Chelants

The hair dyeing composition described herein may further comprise chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996), both incorporated herein by reference.

In an embodiment, the hair dyeing composition may comprise a total amount of chelants ranging from at least about 0.01%, alternatively from about 0.01% to about 5%, alternatively from about 0.25% to about 3%, alternatively from about 0.5% to about 1%, by weight of the total composition.

Suitable chelants include but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively, sodium salts, potassium salts, ammonium salts, and mixtures thereof; alternatively monoethanolammonium salts, diethanolammonium salts, triethanolammonium salts, and mixtures thereof. Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis(2-hydroxybenzyl)ethylenediamine-N,N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N-diacetic acid, aspartic acid-N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety (—PO3H2) or its derivative —PO3R2, wherein $R_2$ is a $C_1$ to $C_6$ alkyl or aryl radical and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylenediamine-tetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N"-ethylenediamine diacetic acid, their salts thereof, their derivatives thereof, and mixtures thereof.

In a specific embodiment, the composition comprises a chelant selected from the group consisting of diethylenetriamine-N,N',N"-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

When the hair dyeing composition is obtained by mixing a tint composition and a developer composition, the chelants may be incorporated in the tint composition and/or in the developer composition. A chelant may be present in the developer composition for stability.

Radical Scavengers

The hair dyeing compositions described herein may comprise a radical scavenger. As used herein the term radical scavenger refers to a species that can react with a radical, to convert the radical species by a series of fast reactions to an unreactive or less reactive species. The radical scavenger is also preferably selected such that it is not an identical species as the alkalising agent and is present in an amount sufficient to reduce the damage to the hair during the colouring/bleaching process. The compositions of the present invention comprise a radical scavenger from about 0.1% to about 10%, preferably from about 1% to about 7% by weight of the radical scavenger relative to the total weight of the composition.

Suitable radical scavengers for use herein may be selected from the classes of alkanolamines, amino sugars, amino acids, esters of amino acids and mixtures thereof. Suitable compounds include 3-substituted-pyrazol-5-ones, 3-carboxy-1H-pyrazol-5-one, 3-methyl-1-phenyl-pyrazol-5-one, 3-methyl-1-p-tolyl-pyrazol-5-one, 3-methyl-1-(4-sulfophenyl)-pyrazol-5-one, 3-methyl-1-(4-sulfoamidophenyl)-pyrazol-5-one, 3-methyl-1-(3-sulfophenyl)-pyrazol-5-one, 3-methyl-1-(3-sulfoamidophenyl)-pyrazol-5-one, 3-methyl-1-(2-chloro-5-sulfophenyl)-pyrazol-5-one, 3-methyl-1-(2,5-dichloro-4-sulfophenyl)-pyrazol-5-one, 3-methyl-1-(4-chlorophenyl)-pyrazol-5-one, 3-methyl-1-(4-carboxyphenyl)-pyrazol-5-one, 3-carboxy-1-phenyl-pyrazol-5-one, 3-carboxy-1-(4-sulfophenyl)-pyrazol-5-one, 1,3-diphenyl-pyrazol-5-one, methyl pyrazol-5-one-3-carboxylate, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, or mixtures thereof, or the salts, such as the potassium, sodium, or ammonium salts thereof, or mixtures thereof. In some embodiments, the inventive compositions may comprise glycine, sarcosine, lysine, serine, 2-methoxyethylamine, glucosamine, glutamic acid, morpholine, piperidine, ethylamine, 3-amino-1-propanol, or mixtures thereof.

pH Modifiers and Buffering Agents

The hair dyeing compositions described herein may further comprise, in addition to the alkalizing agent discussed above, a pH modifier and/or buffering agent in an amount that is sufficiently effective to adjust the pH of the composition to fall within a range from about 3 to about 13, alternatively from about 8 to about 12, alternatively from about 9 to about 11.

Suitable pH modifiers and/or buffering agents include, but are not limited to: ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifiers and/or buffering agents include but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

Thickeners and/or Rheology Modifiers

The hair dyeing compositions described herein may further comprise a thickener in an amount sufficient to provide the composition with a viscosity so that it can be readily applied to the hair without unduly dripping off the hair and causing mess.

In an embodiment, the hair dyeing compositions may comprise a total amount of thickeners ranging from at least about 0.1%, alternatively at least about 1%, alternatively at least about 10%, alternatively at least about 20%, by weight of the total composition.

Suitable thickeners include, but are not limited to: associative polymers, polysaccharides, non-associative polycarboxylic polymers, and mixtures thereof.

As used herein, the expression "associative polymers" means amphiphilic polymers comprising both hydrophilic units and hydrophobic units, for example, at least one C8 to C30 fatty chain and at least one hydrophilic unit. Associative polymers are capable of reversibly combining with each other or with other molecules. Suitable associative thickeners include, but are not limited to: nonionic amphiphilic polymers comprising at least one hydrophilic unit and at least one fatty-chain unit; anionic amphiphilic polymers comprising at least one hydrophilic unit and at least one fatty-chain unit; cationic amphiphilic polymers comprising at least one hydrophilic unit and at least one fatty-chain unit; and amphoteric amphiphilic polymers comprising at least one hydrophilic unit and at least one fatty-chain unit, and mixtures thereof.

Suitable nonionic amphiphilic polymers comprising at least one fatty chain and at least one hydrophilic unit include, but are not limited to: celluloses modified with groups comprising at least one fatty chain (such as hydroxyethylcelluloses modified with groups comprising at least one fatty chain chosen from alkyl, alkenyl and alkylaryl groups); hydroxypropyl guars modified with groups comprising at least one fatty chain; polyether urethanes comprising at least one fatty chain (such as C8-C30 alkyl or alkenyl groups); copolymers of vinylpyrrolidone and of fatty-chain hydrophobic monomers; copolymers of C1-C6 alkyl acrylates or methacrylates and of amphiphilic monomers comprising at least one fatty chain; copolymers of hydrophilic acrylates or methacrylates and of hydrophobic monomers comprising at least one fatty chain, and mixtures thereof. Commercially available anionic materials include those sold as Sepigel 305 by Seppic.

Suitable nonionic amphiphilic polymers comprising at least one hydrophilic unit and at least one fatty-chain unit include, but are not limited to: those polymers comprising at least one fatty-chain allyl ether unit and at least one hydrophilic unit comprising an ethylenic unsaturated anionic monomeric unit (such as a vinylcarboxylic acid unit, particularly a unit chosen from units derived from acrylic acids, methacrylic acids, and mixtures thereof), wherein the fatty-chain allyl ether unit corresponds to the monomer of formula (XV) below $$CH_2=C(R1)CH_2OB_nR \qquad (XV)$$

in which R1 is chosen from H and CH3, B is an ethyleneoxy radical, n is chosen from zero and integers ranging from 1 to 100, R is chosen from hydrocarbon-based radicals chosen from alkyl, alkenyl, arylalkyl, aryl, alkylaryl and cycloalkyl radicals, comprising from 8 to 30 carbon atoms, and, further, for example, from 10 to 24 carbon atoms and even further, for example, from 12 to 18 carbon atoms.

Suitable anionic amphiphilic polymers include, but are not limited to: those polymers comprising at least one hydrophilic unit of unsaturated olefinic carboxylic acid type, and at least one hydrophobic unit of the type such as a (C8-C30) alkyl ester or (C8-C30) oxyethylenated alkyl ester of an unsaturated carboxylic acid, wherein the hydrophilic unit of unsaturated olefinic carboxylic acid type corresponds to, for example, the monomer of formula (XVI) below $$CH2=C(R1)COOH \qquad (XVI)$$

in which R1 is chosen from H, CH3, C2H5 and CH2COOH (i.e. acrylic acid, methacrylic, ethacrylic and itaconic acid units); and wherein the hydrophobic unit of the type such as a (C8-C30) alkyl ester or (C8-C30) oxyethylenated alkyl ester of an unsaturated carboxylic acid corresponds to, for example, the monomer of formula (XVII) below $$CH2=C(R1)COOBnR2 \qquad (XVII)$$

in which R1 is chosen from H, CH3, C2H5 and CH2COOH (i.e. acrylate, methacrylate, ethacrylate and itaconate units), B is an ethyleneoxy radical, n is chosen from zero and integers ranging from 1 to 100, R2 is chosen from C8-C30 alkyl radicals, for example, C12-C22 alkyl radical. Anionic amphiphilic polymers may further be cross-linked. The crosslinking agent can be a monomer comprising a group (XVIII) below $$CH2=C< \qquad (XVIII)$$

with at least one other polymerizable group whose unsaturated bonds are not conjugated with respect to one another. Mention may be made, for example, of polyallyl ethers such as polyallylsucrose and polyallyl pentaerythritol.

Suitable cationic amphiphilic polymers include but are not limited to: quaternized cellulose derivatives and polyacrylates comprising amino side groups. The quaternized cellulose derivatives are, for example, chosen from quaternized celluloses modified with groups comprising at least one fatty chain, such as alkyl, arylalkyl and alkylaryl groups comprising at least 8 carbon atoms, and mixtures thereof, quaternized hydroxyethylcelluloses modified with groups comprising at least one fatty chain, such as alkyl, arylalkyl and alkylaryl groups comprising at least 8 carbon atoms, and mixtures thereof. The alkyl radicals borne by the above quaternized celluloses and hydroxyethylcelluloses, for example, contain from 8 to 30 carbon atoms. The aryl radicals, for example, are chosen from phenyl, benzyl, naphthyl and anthryl groups.

Suitable amphoteric amphiphilic polymers comprising at least one hydrophilic unit and at least one fatty-chain unit, may be made, for example, of methacrylamidopropyltrimethylammonium chloride/acrylic acid/C8-C30 alkyl methacrylate copolymers, wherein the alkyl radical is, for example, a stearyl radical.

In an embodiment, the associative polymers may comprise at least one hydrophilic unit which is unsaturated carboxylic acid or its derivatives, and at least one hydrophobic unit which is a C8 to C30 alkyl ester or oxyethylenated C8-C30 alkyl ester of unsaturated carboxylic acid. The unsaturated carboxylic acid is preferably acrylic acid, methacrylic acid or itaconic acid. Commercially available materials include those sold as Aculyn-22 by Rohm & Haas; Permulen TR1, Carbopol 2020, Carbopol Ultrez-21/-30 by Noveon, Structure 2001/3001 by National Starch. Other preferred associative polymers include polyether polyurethane, commercially available as Aculyn-44/-46 by Rohm and Haas. Further preferred associative polymers include cellulose modified with groups comprising at least one C8-C30 fatty chain, commercially available under the trade name Natrosol Plus Grade 330 CS by Aqualon.

Suitable non-associative cross-linked polycarboxylic polymers include but are not limited to: cross-linked acrylic acid homopolymers, copolymers of acrylic or (meth)acrylic acid and of C1-C6 alkyl acrylate or (meth)acrylate, and mixtures thereof. Commercially available materials include those sold as Carbopol 980/981/954/1382/2984/5984 by Noveon, Synthalen M/Synthalen L/Synthalen K/Synthalen C R by 3V, Aculyn-33 by Rohm and Haas.

Suitable polysaccharides include, but are not limited to: glucans, modified and unmodified starches (such as those derived, for example, from cereals, for instance wheat, corn or rice, from vegetables, for instance yellow pea, and tubers, for instance potato or cassaya), amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacantha, ghatti gums, karaya gums, carob gums, galactomannans, such as guar gums, and non-ionic derivatives thereof (hydroxypropyl guar) and biopolysaccharides, such as xanthan gums, gellan gums, welan gums, scleroglucans, succinoglycans, and mixtures thereof. Suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328, 1980, and in "Industrial Gums—Polysaccharides and their Derivatives", edited by Roy L. Whistler, Second Edition, published by Academic Press Inc., all three being incorporated herein by reference. A preferred polysaccharide is a bio-polysaccharide, particularly bio-polysaccharides selected from xanthan gum, gellan gum, welan gum, scleroglucan or succinoglycan; commercially available as Keltrol® T by Kelco and Rheozan® by Rhodia Chimie. Another preferred polysaccharide is hydroxypropyl starch derivative, particularly hydroxypropyl starch phosphate, commercially available as Structure XL® by National Starch, a hydrophobically modified cellulose derivative, commercially available as Structure® Cel 500 HM by AkzoNobel.

Commercially available salt-tolerant thickeners include, but not limited to: xanthan, guar, hydroxypropyl guar, scleroglucan, methyl cellulose, ethyl cellulose (commercially available as Aquacote), hydroxyethyl cellulose (Natrosol), carboxymethyl cellulose, hydroxypropylmethyl cellulose, microcrystalline cellulose, hydroxybutylmethyl cellulose, hydroxypropyl cellulose (Klucel), hydroxyethyl ethyl cellulose, cetyl hydroxyethyl cellulose (Natrosol Plus 330), polyvinylpyrrolidone (Povidone, FlexiThix™), Acrylates/Ceteth-20 Itaconate Copolymer (Structure 3001), hydroxypropyl starch phosphate (Structure ZEA), polyethoxylated urethanes or polycarbamyl polyglycol ester such as PEG-150/Decyl/SMDI copolymer (Aculyn 44), PEG-150/Stearyl/SMDI copolymer (Aculyn 46), trihydroxystearin (Thixcin), acrylates copolymer (Aculyn 33) or hydrophobically modified acrylate copolymers (such as Acrylates/Steareth-20 Methacrylate Copolymer as Aculyn 22), acrylates/steareth-20 methacrylate crosspolymer (Aculyn 88), acrylates/vinyl neodecanoate crosspolymer (Aculyn 38), acrylates/beheneth-25 methacrylate copolymer (Aculyn 28), acrylates/C10-30 alkyl acrylate crosspolymer (Carbopol ETD 2020), non-ionic amphophilic polymers comprising at least one fatty chain and at least one hydrophilic unit selected from polyether urethanes comprising at least one fatty chain, blends of Ceteth—10 phosphate, Dicetyl phosphate and Cetearyl alcohol (available as Crodafos CES), and mixtures thereof.

Salt

In an embodiment, cosmetically acceptable salt, such as ammonium, sodium or potassium salts with appropriate counter ions, may be added to the hair dyeing compositions described herein to act as leveling agents to minimize patchy coloring results.

Carbonate Ion Sources

The hair dyeing compositions described herein may further comprise a source of carbonate ions, carbamate ions, hydrogen carbonate ions, and mixtures thereof in a sufficient amount to reduce damage to the hair during the coloring process.

In an embodiment, the hair dyeing compositions may comprise a total amount of a carbonate ion source ranging from about 0.1% to about 15%, alternatively from about 0.1% to about 10%, alternatively from about 1% to about 7%, by weight of the total composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof, alternatively sodium hydrogen carbonate, potassium hydrogen carbonate, and mixtures thereof; alternatively ammonium carbonate, ammonium hydrogen carbonate, and mixtures thereof.

Conditioning Agents

The hair dyeing compositions described herein may further comprise a conditioning agent, and/or be used in combination with a composition comprising a conditioning agent.

In an embodiment, the hair dyeing compositions may comprise a total amount of conditioning agents ranging from about 0.05% to about 20%, alternatively from about 0.1% to about 15%, alternatively from about 0.2% to about 10%, alternatively from about 0.2% to about 2%, alternatively from about 0.5% to 2%, by weight of the total composition. The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol.

Particularly useful conditioning materials may be cationic polymers. Conditioners of cationic polymer type can be chosen from those comprising units of at least one amine group chosen from primary, secondary, tertiary and quaternary amine groups that may either form part of the main polymer chain, or be borne by a side substituent that is directly attached to the main polymer chain, described hereinafter.

Suitable silicones include, but are not limited to: polyalkylsiloxane oils, linear polydimethylsiloxane oils containing trimethylsilyl or hydroxydimethylsiloxane endgroups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain and mixtures thereof. Said organofunctional group(s) may be selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of a pre-formed emulsion. Suitable silicones also include: silicones containing groups that may be ionized into cationic groups, for example aminosilicones containing at least 10 repeating siloxane $(Si(CH_3)_2$—O) units within the polymer chain, with either terminal, graft, or a mixture of terminal and graft aminofunctional groups. Example functional groups are not limited to aminoethylaminopropyl, aminoethylaminoisobutyl, aminopropyl. In the case of graft polymers, the terminal siloxane units can be $(CH_3)_3Si$—O, $R_{12}(CH_3)_2Si$—O, where $R_{12}$ can be either OH or $OR_{13}$, where $R_{13}$ is a C1-C8 alkyl group, or a mixture of both terminal groups. These silicones are also available as preformed emulsions. Commercially available aminosilicones include those sold as DC-2-8566, DC 7224, DC-2-8220 by Dow Corning; SF1708, SM2125 by GE Silicones; Wacker Belsil ADM 653/ADM 1100/ADM 1600/ADM 652/ADM 6057E/ADM 8020 by Wacker Silicones; DC929, DC939, DC949 by Dow Corning; SM2059 by GE Silicones. Suitable aminosilicones may also contain additional functional groups, particularly additional functional groups including polyoxyalkylene, the reaction product of amines and carbinols, and alky chains. Commercially available materials are known as methoxy PEG/PPG-7/3 Aminopropyl Dimethicone (e.g. Abil Soft AF100, by Degussa), or as Bis(C13-15 Alkoxy)PG Amodimethicone (e.g. DC 8500, by Dow Corning).

Suitable cationic polymers include but are not limited to: polymers comprising units of at least one amine group chosen from primary, secondary, tertiary and quaternary amine groups that may either form part of the main polymer chain or be borne by a side substituent that is directly attached to the main polymer chain. Such cationic polymers generally have a number average molecular mass ranging from about 500 to about $5 \times 10^6$, alternatively from about 1000 to about $3 \times 10^6$. Preferably the cationic polymers are selected from polymers of the polyamine, polyamino amide and polyquaternary ammonium type.

Suitable polymers of the polyamine, polyamino amide and polyquaternary ammonium type include, but are not limited to:

1) Homopolymers and copolymers derived from acrylic or methacrylic esters or amides. Copolymers of these polymers may also comprise at least one unit derived from comonomers which may be chosen from the family of acrylamides, methacrylamides, diacetone acylamides, acrylamides and methacrylicamides substituted on the nitrogen with at least one group chosen from lower (C1-$C_4$) alkyls, acrylic and methacrylic acids and esters thereof, vinylactams such as vinlypyrrolidone and vinylcaprolactam, and vinyl esters. Suitable examples include copolymers of acrylamide and of methacryloyloxyethyltrimethylammonium methosulfate, including polymers known as Polyquaternium-5 (e.g. commercially available under the trade name Reten 210/220/230/240/1104/1105/1006 by Hercules; Merquat 5/5 SF by Nalco); copolymers of vinylpyrrolidone and dimethylaminopropyl methacrylamide, including polymers known as Polyquaternium-28 (e.g. Gafquat HS-100 by ISP); copolymers of vinyl pyrrolidone and dialkyaminoalkyl acrylates or methactylates, including polymers known as Polquaternium-11 (see Gafquat 440/734/755/755N by ISP; Luviquat PQ11 PM by BASF; Polyquat-11 SL by Sino Lion); copolymers vinylpyrrolidone, dimethylaminopropyl methacrylamide and methacryloylaminopropyl lauryldimonium chloride, including polymers known as polyquaternium-55 (e.g. Styleze W-20 by ISP); copolymers of acrylic acid, acrylamide and methacrylamidopropyltrimonium chloride, including polymers known as Polyquaternium-53 (e.g. Merquat 2003 by Nalco); copolymers of dimethyaminopropylacrylate (DMAPA), acrylic acid and acrylonitrogens and diethyl sulphate, including polymers known as Polyquaternium-31 (e.g. Hypan QT100 by Lipo); copolymers of acrylamide, acrylamidopropyltrimonium chloride, 2-amidopropylacrylamide sulfonate, and dimethyaminopropylacrylate (DMAPA), including polymers known as polyquaternium-43 (e.g. Bozequat 4000 by Clairant); copolymers of acrylic acid, methylacrylate and methacrylamidopropyltrimonium chloride, including polymers known as Polyquaternium-47 (e.g. Merquat 2001/2001N by Nalco); copolymers of methacryloyl ethyl betaine, 2-hydroxyethyl methacrylate and methacryloyl ethyl trimethyl ammonium chloride, including polymers known as Polyquaternium-48 (e.g. Plascize L-450 by Goo Chemical); copolymers of acrylic acid diallyl dimethyl ammonium chloride and acrylamide, including polymers known as polyquaternium-39 (e.g. Merquat 3330/3331 by Nalco). Further suitable examples include copolymers of methacrylamide methacrylamido-propyltrimonium and methacryloylethyltrimethyl ammonium chloride and their derivatives, either homo or copolymerised with other monomers, including polymers known as Polyquaternium-8, Polyquaternium-9, Polyquaternium-12, Polyquaternium-13 Polyquaternium-14, Polyquaternium-15 (e.g. Rohagit KF 720 F by Rohm), Polyquaternium-30 (e.g. Mexomere PX by Chimex), Polyquaternium-33, Polyquaternium-35, Polyquaternium-36 (e.g. Plex 3074 L by Rhon), Polyquaternium 45 (e.g. Plex 3073L by Rohn), Polyquaternium 49 (e.g. Plascize L-440 by Goo Chemicals), Polyquaternium 50 (e.g. Plascize L-441 by Goo Chemicals), Polyquaternium-52.

2) Cationic polysaccharides, such as cationic celluloses and cationic galactomannan gums. Among the cationic polysaccharides that maybe mentioned, for example, are cellulose ether derivatives comprising quaternary ammonium groups and cationic cellulose copolymers or cellulose derivatives grafted with a water-soluble quaternary ammonium monomer and cationic galactomannan gums. Suitable examples include copolymers of hydroxyethylcelluloses and diallyldimethyl ammonium chlorides, including polymers known as Polyquaternium-4 (e.g. Celquat L 200 and Celquat H 100 by National Starch); copolymers of hydroxyethylcelluloses and a trimethyl ammonium substituted epoxide, including polymers known as Polyquaternium-10 (e.g. AEC Polyquaternium-10 by A&E Connock; Catinal C-100/HC-35/HC-100/HC-200/LC-100/LC-200 by Toho; Celquat SC-240C/SC-230M by National Starch; Dekaquat 400/3000 by Dekker; Leogard GP by Akzo Nobel; RITA Polyquat 400/3000 by RITA; UCARE Polymer JR-125/JR-400/JR-30M/LK/LR 400/LR 30M by Amerchol); copolymers of hydroxyethylcelluloses and lauryl dimethyl ammonium substituted epoxides, including polymers known as Polyquaternium-24 (e.g. Quatrisoft polymer LM-200 by Amerchol); derivatives of hydroxypropyl guar, including polymers as guar hydroxypropyltrimonium chloride (e.g. Catinal CG-100, Catinal CG-200 by Toho; Cosmedia Guar C-261N, Cosmedia Guar C-261N, Cosmedia Guar C-261N by Cognis; DiaGum P 5070 by Freedom Chemical Diamalt; N-Hance Cationic Guar by Hercules/Aqualon; Hi-Care 1000, Jaguar C-17, Jaguar C-2000, Jaguar C-13S, Jaguar C-14S, Jaguar Excel by Rhodia; Kiprogum CW, Kiprogum NGK by Nippon Starch); hydroxypropyl derivatives of guar hydroxypropyltrimonium chloride, including polymers known as hydroxypropyl guar hydroxypropyltrimonium chloride (e.g. Jaguar C-162 by Rhodia).

3) Polyamino amide derivatives resulting from the condensation of polyalkylene polyamines with polycarboxylic acids followed by alkylation with difunctional agents. Among the derivative, mention may be made for example to adipic acid/dimethylaminohydroxypropyl/diethylenetriamine.

4) Polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Suitable examples include the polymer adipic acid/epxoypropyl/diethylenetriamine.

5) Cyclopolymers of dialkdiallylamine or of dialkyldiallyammonium, including: Dimethyldiallyammonium chloride polymers, including polymers known as Polyquaternium-6 (e.g. Merquat 100 by Nalco; Mirapol 100 by Rhodia; Rheocare CC6 by Cosmetic Rheologies; AEC polyquaternium-6 by A&E Connock; Agequat 400 by CPS; Conditioner P6 by 3V Inc.; Flocare C106 by SNF; Genamin PDAC by Clariant; Mackernium 006 by McIntyre); copolymers of acrylamides and dimethyldiallylammonium chlorides monomers, including polymers known as Polyquaternium-7 (e.g. AEC Polyquaternium-7 by A&E Connock; Agequat-5008/C-505 by CPS; Conditioner P7 by 3V Inc.; Flocare C 107 by SNF; Mackernium 007/007S by McIntyre; ME Polymer 09W by Toho; Merquat 550/2200/S by Nalco; Mirapol 550 by Rhodia; Rheocare CC7/CCP7 by Cosmetic Rheologies; Salcare HSP-7/SC10/Super 7 by Ciba); copolymers of dimethyldiallylammoniumchlorides and acrylic acids, including polymers known as polyquaternary-22 (e.g. Merquat 280/Merquat 295 by Nalco).

6) Quaternary diammonium polymers comprising repeat units corresponding to [-N+(R1)(R2)–A1–N+(R3)(R4)–B1-][2X-], in which R1, R2, R3 and R4, which may be identical or different, are chosen from aliphatic, alicyclic and arylaliphatic radicals comprising from 1 to 20 carbon atoms and from lower hydroxyalkylaliphatic radicals, or R1, R2, R3 and R4, together or separately, constitute, with the nitrogen atoms to which they are attached, heterocycles optionally comprising a second heteroatom other then nitrogen, or R1, R2, R3 and R4, are chosen from liner or branched C1-C6 alkyl radicals substituted with at least one group chosen from nitrile, ester, acyl and amide groups and groups of —CO—O—R5-D and —CO—NH—R5-D wherein R5 is chosen from alkylene groups and D is chosen from quaternary ammonium groups. A1 and B1, which may be identical or different, are chosen from linear and branched, saturated or unsaturated polymethylene groups comprising 2 to 20 carbon atoms. The polymethylene groups may comprise, linked to or intercalated in the main ring, at least one entity chosen from aromatic rings, oxygen and sulphur atoms and sulphoxide, sulphone, disulphide, amino, alkylamino, hydroxyl, quaternary, ammonium, ureido, amide and ester groups, and X- is an anion derived from inorganic and organic acids. D is chosen from a glycol residue, a bis-secondary diamine residue, a bis-primary diamine residue or a ureylene group. Suitable examples include polymers known as Hexadimethrine chloride, where R1, R2, R3 and R4 are each methyl radicals, A1 is (CH2)3 and B1 is (CH2)6 and X=Cl; as polyquaternium-34 where R1 and R2 are ethyl radicals and R3 and R4 are methyl radicals and A1 is (CH2)3 and B1 is (CH2)3 and X=Br (e.g. Mexomere PAX by Chimax).

7) Polyquaternary ammonium polymers comprising repeating units of formula [—N+(R6)(R7)—(CH2)r-NH—CO—(CH2)q-(CO)t-NH—(CH2)s-N+(R8)(R9)-A-][2X-], in which R6, R7, R8 and R9 which may be identical or different, are chosen from a hydrogen atom and a methyl, ethyl, propyl, hydroxyethyl, hydroxypropyl, and —CH2CH2(OCH2CH2)pOH radicals, wherein p is equal to 0 or an integer ranging from 1 to 6, wherein R6, R7, R8 and R9 do not all simultaneously represent a hydrogen atom. R and s which maybe identical or different are each an integer ranging from 1 to 6, q is equal to 0 or an integer ranging from 1 to 34 and X- is anion such as a halide. T is an integer chosen to be equal to 0 or 1. A is chosen from divalent radicals such as —CH2-CH2-O—CH2-CH2-. Suitable examples include: polymers known as polyquaternium-2, where r=s=3, q=0, t=0, R6, R7, R8 and R9 are methyl groups, and A is —CH2-CH2-O—CH2-CH2; as CH2-CH2O—CH2-CH2 (e.g. Ethpol PQ-2 from Ethox; Mirapol A-15 by Rhodia); as polyquaternium-17 where r=s=3, q=4, t=1 R6, R7, R8 and R9 are methyl groups, and A is —CH2-CH2-O—CH2-CH2; as Polyquaternium 18, where r=s=3, q=7, t=1 R6, R7, R8 and R9 are methyl groups, and A is —CH2-CH2-O—CH2-CH2; as the block copolymer formed by the reaction of Polyquaternium-2 with Polyquaternium-17, which are known as Polyquaternium 27 (e.g. Mirapol 175 by Rhodia).

8) Copolymers of vinylpyrrolidones and of vinylimidazoles and optionally vinylcaprolactums, including polymers known as Polyquaternary-16 formed from methylvinylimidazolium chlorides and vinylpyrrolidones (e.g. Luviquat FC370//FC550/FC905/HM-552 by BASF); copolymers of vinylcaprolactams and vinylpyrrolidones with methylvinylimidazolium methosulfates, including polymers known as Polyquaternium-46 (e.g. Luviquat Hold by BASF); copolymers of vinylpyrrolidones and quaternized imidazolines, including polymers known as polyquaternary 44 (e.g. Luviquat Care by BASF).

9) Polyamines such as Polyquart H sold by Cognis under the reference name polyethylene glycol (15) tallow polyamine.

10) Cross linked methacryloyloxy(C1-C4)alkyltri(C1-C4)alkylammonium salt polymers such as the polymers obtained by homopolymerisation of dimethylaminoethyl methacrylates quaternized with methyl chloride, or by copolymerisation of acrylamides with dimethylaminoethyl methacrylates quaternized with methyl chloride, the homo or copolymerisation being followed by crosslinking with a compound comprising olefinic unsaturation, such as methylenebisacrylamides, including polymers known as Polyquaternium-37 (e.g. Synthalen CN/CR/CU sold by 3V sigma; or as a dispersion in another media such as Salcare SC95/SC96 by Ciba; Rheocare CTH(E) by Cosmetic Rheologies) and polymers known as Polyquaternium-32 (e.g. sold as a dispersion in mineral oil such as Salcare SC92 by Ciba).

11) Further examples of cationic polymers include polymers known as Polyquaternium 51 (e.g. Lipidure-PMB by NOF), as Polyquaternium 54 (e.g. Qualty-Hy by Mitsui), as Polyquaternium 56 (e.g. Hairrol UC-4 by Sanyo chemicals), as Polyquaternium 87 (e.g. Luviquat sensation by BASF).

12) Silicone polymers comprising cationic groups and/or groups which may be ionised into cationic groups. Suitable examples include cationic silicones of the general formula (R10-N+(CH3)2)-R11-(Si(CH3)2-O)x-R11-(N+(CH3)2)-R10), where R10 is an alkyl derived from coconut oil, and R11 is (CH2CHOCH2O(CH2)3 and x is a number between 20 and 2000, including polymers known as Quaternium 80 (e.g. Abil Quat 3272/3474 sold by Goldschmidt); silicones containing groups which may be ionised into cationic groups, for example aminosilicones containing at least 10 repeating siloxane—(Si(CH3)2-O) units within the polymer chain, with either terminal, graft or a mixture of terminal and graft aminofunctional groups. Example functional groups are not limited to aminoethylaminopropyl, aminoethylaminoisobutly, aminopropyl. In the case of graft polymers, the terminal siloxane units can either be (CH3)3Si—O or R12(CH3)2Si—O, where R12 can be either OH or OR13, where R13 is a C1-C8 alky group, or a mixture of both functional terminal groups. These silicones are also available as preformed emulsions. Polymer with terminal siloxane units of (CH3)3Si—O examples includes polymers known as trimethylsilylamodimethicone (e.g. DC-2-8566, DC 7224, DC-2-8220 by Dow Corning; SF1708, SM 2125 GE Silicones; Wacker Belsil ADM 653 by Wacker silicones). Further examples include polymers with terminal siloxane units of (R12O)(CH3)2Si—O where R12 can be either OH or OR13, where R13 is a C1-C8 alky group, or a mixture of both functional terminal groups, known as amodimethicone (e.g. Wacker Belsil ADM 1100/ADM 1600/ADM 652/ADM 6057E/ADM 8020 by Wacker Silicones; DC929, DC939, DC949 by Dow Corning; SM2059 by GE silicones). Silicones containing groups which may be ionised into cationic groups—for example silicones containing at least 10 repeating siloxane—(Si(CH3)2-O) units within the polymer chain, with either terminal, graft or a mixture of terminal and graft aminofunctional groups, together with additional functional groups. Additional functional groups can include polyoxyalkylene, the reaction product of amines and carbinols, alky chains. For example, products known as methoxy PEG/PPG-7/3 Aminopropyl Dimethicone (e.g. Abil Soft AF100 by Degussa). For example, products known as Bis (C13-15 Alkoxy) PG Amodimethicone (e.g. DC 8500 by Dow Corning).

In an embodiment, the cationic polymer is selected from the group consisting of polyquaternium 37, polyquaternium 7, polyquaternium 22, polyquaternium 87, and mixtures thereof; alternatively from the group consisting of polyquaternium 37, polyquaternium 22, and mixtures thereof.

Surfactants

The hair dyeing compositions described herein may further comprise a surfactant. Suitable surfactants generally have a lipophilic chain length of from about 8 to about 30 carbon atoms and can be selected from anionic surfactants, nonionic surfactants, amphoteric surfactants, cationic surfactants, and mixtures thereof.

In an embodiment, the hair dyeing compositions may comprise a total amount of surfactants ranging from about 0.01% to about 60%, alternatively from about 0.05% to about 30%, alternatively from about 0.1% to about 25%, alternatively from about 0.1% to about 20%, by weight of the total composition.

The compositions may comprise a mixture of an anionic surfactant and an amphoteric surfactant with one or more nonionic surfactants. The composition may comprise a total amount of anionic surfactant ranging from about 0.01% to about 20%, alternatively from about 0.05% to about 15%, alternatively from about 0.1% to about 15%, by weight of the total composition; and a total amount of amphoteric and/or nonionic components, which may range independently from each other from about 0.01% to about 15%, alternatively from about 0.05% to about 10%, alternatively from about 0.1% to about 8%, by weight of the total composition.

Suitable anionic surfactants include, but are not limited to: salts (such as alkaline salts, for example, sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, a-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates; N-acyltaurates; and mixtures thereof. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof. Anionic derivatives of polysaccharides, for example carboxyalkyl ether of alkyl polyglucosides, can be also used.

Nonionic surfactants are compounds that are well known (see, for example, in this respect "Handbook of Surfactants" by M. R. Porter, published by Blackie & Son (Glasgow and London), 1991, pp. 116-178). Suitable non-ionic surfactants include, but are not limited to: polyethoxylated, polypropoxylated and polyglycerolated fatty acids, alkyl phenols, α-diols and alcohols comprising a fatty chain comprising, for example, from 8 to 18 carbon atoms, it being possible for the number of ethylene oxide or propylene oxide groups to range, for example, from 2 to 200 and for the number of glycerol groups to range, for example, from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide and their momoethanolamine and diethanolamine derivatives, polyglycerolated fatty amides, for example, comprising on average from 1 to 5, and such as from 1.5 to 4, glycerol groups; polyethoxylated fatty amines such as those containing from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides.

Suitable amphoteric surfactants include, but are not limited to: aliphatic secondary and tertiary amine derivatives in which the aliphatic radical is chosen from linear and branched chains comprising from 8 to 22 carbon atoms and comprising at least one water-soluble anionic group (for example carboxylate, sulphonate, sulphate, phosphate or phosphonate); mention may also be made of ($C_8$-$C_{20}$)alkylbetaines, sulphobetaines, ($C_8$-$C_{20}$)alkylamido($C_1$-$C_6$)alkylbetaines or ($C_8$-$C_{20}$)alkylamido($C_1$-$C_6$)alkylsulphobetaines. Among the amine derivatives, mention may be made of the products sold as Miranol, as described, for example, in U.S. Pat. Nos. 2,528,378 and 2,781,354 and having the structures of: $R_2$—CON HCH$_2$CH$_2$—N$^+$($R_3$)($R_4$)(CH$_2$COO$^-$), (XIX) in which: $R_2$ is chosen from alkyl radicals derived from an acid $R_2$—COOH present in hydrolysed coconut oil, and heptyl, nonyl and undecyl radicals, $R_3$ is a β-hydroxyethyl group and $R_4$ is a carboxymethyl group; and of $R_5$—CONHCH$_2$CH$_2$—N(B)(C) (XX) wherein B represents —CH$_2$CH$_2$OX', C represents —(CH$_2$)$_z$—Y', with z=1 or 2, X' is chosen from the —CH$_2$CH$_2$—COOH group and a hydrogen atom, Y' is chosen from —COOH and —CH$_2$—CHOH—SO$_3$H radicals, $R_5$ is chosen from alkyl radicals of an acid $R_5$—COOH present in coconut oil or in hydrolysed linseed oil, alkyl radicals, such as $C_7$, $C_9$, $C_{11}$ and $C_{13}$ alkyl radicals, a $C_{17}$ alkyl radical and its iso form, and unsaturated $C_{17}$ radical. These compounds are classified in the CTFA dictionary, 5$^{th}$ edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid. Salts of diethyl aminopropyl cocoaspartamid can be also used.

Suitable cationic surfactants include, but are not limited to, the quaternary ammonium salts A) to D) as defined hereinafter:

A) Quaternary ammonium salts of general formula (IX) below:

(IX)

wherein X$^-$ is an anion chosen from halides (chloride, bromide and iodide), ($C_2$-$C_6$)alkyl sulphates, such as methyl sulphate, phosphates, alkyl and alkylaryl sulphonates, and anions derived from organic acids, such as acetate and lactate, and wherein $R_1$ to $R_4$ are as below in i) or ii).

i) Radicals $R_1$ to $R_3$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from: alkyl, alkoxy and alkylamide radicals. $R_4$ is chosen from linear and branched alkyl radicals comprising from 16 to 30 carbon atoms. A suitable cationic surfactant is, for example, a behenyltrimethylammonium salt (for example chloride).

ii) Radicals $R_1$ and $R_2$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from alkyl, alkoxy, alkylamide and hydroxyalkyl radicals comprising from about 1 to 4 carbon atoms. Radicals $R_3$ and $R_4$, which may be identical or different, are chosen from linear and branched alkyl radicals comprising from 12 to 30 carbon atoms, the said alkyl radicals comprise at least one function chosen from ester and amide functions. $R_3$ and $R_4$ may be chosen from $(C_{12}\text{-}C_{22})$alkylamido$(C_2\text{-}C_6)$alkyl and $(C_{12}\text{-}C_{22})$ alkylacetate radicals. A suitable cationic surfactant is, for example, a dicetyldimethyl ammonium salt (for example chloride);

B) Quaternary ammonium salts of imidazolinium of formula (XI) below:

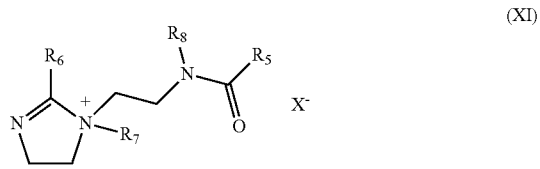

in which $R_5$ is chosen from alkenyl and alkyl radicals comprising from 8 to 30 carbon atoms, for example fatty acid derivatives of tallow, $R_6$ is chosen from a hydrogen atom, $C_1$-$C_4$ alkyl radicals and alkenyl and alkyl radicals comprising from 8 to 30 carbon atoms, $R_7$ is chosen from $C_1$-$C_4$ alkyl radicals, $R_8$ is chosen from a hydrogen atom and $C_1$-$C_4$ alkyl radicals, and $X^-$ is an anion chosen from halides, phosphates, acetates, lactates, alkyl sulphates, alkyl sulphonates and alkylaryl sulphonates. In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Such a product is, for example, Quaternium-27 (CTFA 1997) or Quaternium-83 (CTFA 1997), commercially available as "Rewoquat®" W75/W90/W75PG/W75HPG by Witco.

C) Diquaternary ammonium salts of formula (XII):

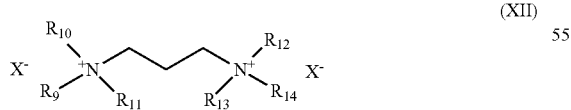

in which $R_9$ is chosen from aliphatic radicals comprising from about 16 to 30 carbon atoms, $R_{10}$, $R_{11}$, $R_{12}$, $R_{13}$ and $R_{14}$, which may be identical or different, are chosen from hydrogen and alkyl radicals comprising from 1 to 4 carbon atoms, and $X^-$ is an anion chosen from halides, acetates, phosphates, nitrates and methyl sulphates. Such diquaternary ammonium salts, for example, include propanetallowdiammonium dichloride.

D) Quaternary ammonium salts comprising at least one ester function, of formula (XIII) below:

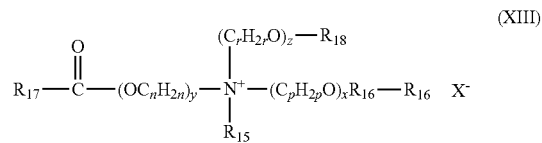

in which: $R_{15}$ is chosen from C1-C6 alkyl radicals and C1-C6 hydroxyalkyl and dihydroxyalkyl radicals; R16 is chosen from: a radical R19C(O)—, linear and branched, saturated and unsaturated C1-C22 hydrocarbon-based radicals R20, and a hydrogen atom, R18 is chosen from: a radical R21C(O)—, linear and branched, saturated and unsaturated C1-C6 hydrocarbon-based radicals R22, and a hydrogen atom, R17, R19 and R21, which may be identical or different, are chosen from linear and branched, saturated and unsaturated C7-C21 hydrocarbon-based radicals; n, p and r, which may be identical or different, are chosen from integers ranging from 2 to 6; y is chosen from integers ranging from 1 to 10; x and z, which may be identical or different, are chosen from integers ranging from 0 to 10; X- is an anion chosen from simple and complex, organic and inorganic anions; with the proviso that the sum x+y+z is from 1 to 15, that when x is 0, then R16 is R20 and that when z is 0, then R18 is R22. In one embodiment, the ammonium salts of formula (XXXXI) can be used, in which: R15 is chosen from methyl and ethyl radicals, x and y are equal to 1; z is equal to 0 or 1; n, p and r are equal to 2; R16 is chosen from: a radical R19C(O)—, methyl, ethyl and C14-C22 hydrocarbon-based radicals, and a hydrogen atom; R17, R19 and R21, which may be identical or different, are chosen from linear and branched, saturated and unsaturated C7-C21, hydrocarbon-based radicals; R18 is chosen from: a radical R21C(O)— and a hydrogen atom. Such compounds are commercially available as Dehyquart by Cognis, Stepanquat by Stepan, Noxamium by Ceca, and Rewoquat WE 18 by Rewo-Witco.

Form of the Hair Dyeing Compositions

The hair dyeing compositions described herein may be formed as thick liquid, cream, gel, emulsion, foam, aerosol mousse or as a solid form to which water is added to generate the oxidant and form a thickened vehicle suitable for hair dyeing.

Method for Dyeing Keratin Fibers

In a fourth aspect, the present invention relates to a method for dyeing keratin fibers, comprising the following steps:
  (a) providing a tint composition comprising a coupler being a 4-amino-indole compound of formula
    (I), according to claim 9; and, a developer;
  (b) providing an oxidizing composition comprising an oxidizing agent;
  (c) combining the tint composition and the oxidizing composition to form a hair dyeing composition;
  (d) contacting hair with the hair dyeing composition.

Hair Dyeing Kit

In a fifth aspect, the present invention relates to a hair dyeing kit, comprising:
  (a) An individually packaged oxidizing composition comprising an oxidizing agent;
  (b) An individually packaged tint composition comprising a coupler being a 4-amino-indole compound of formula
    (I), according to the claim 9; and, a developer.

The hair dyeing compositions usually are sold in kits comprising, in individually packaged components such as separate containers, a tint composition (also called "dye cream" for emulsions or "dye liquid" for solutions) comprising the oxidative dye precursors and an optional alkalizing agent in a suitable carrier, and; an oxidizing composition (also called "hydrogen peroxide cream" for emulsions or "hydrogen peroxide liquid" for solutions) comprising the oxidizing agent. The consumer mixes the tint composition and oxidizing composition together immediately before use to form a hair coloring composition and applies the hair coloring composition onto the hair. An alternative embodiment wherein the tint composition is provided in a solid form and mixed with a liquid oxidizing composition prior to application to the hair may also be utilized.

The tint and oxidizing compositions may be, independently from one another, prepared as so called thin liquids or creams. Typically, thin type liquids have a viscosity of less than 1,000 cPs. Upon mixing the component parts, the resultant hair coloring or bleaching compositions preferably have a viscosity of from 1,000 to 60,000 cPs, more preferably from 2,000 to 30,000 cPs and most preferably from 3,000 to 25,000 cPs. Viscosity is measured using Brookfield viscometers with cone and plate attachment. For viscosities in the range of 0 to 12,000 cPs the Brookfield DV-11 viscometer with S42 plate is used. 2 ml sample of the composition is equilibrated at 26.7° C. for three minutes before the readings are taken at 1 rpm. For viscosities in the range of 12,000 to 60,000 cPs the Brookfield DV-1 viscometer with S52 plate is used. 0.5 ml sample of the composition is equilibrated for 1 minute at 26.7° C. before the readings are taken at 1 rpm.

Application of the hair dyeing composition to the hair may be undertaken in several ways. Application of the hair colorant composition may take place on the whole head of hair of an end user. By "whole head of hair" it is meant that the hair all over the head from the root of the hair to the tip of the hair is included in the application process. By contrast, the application of the hair colorant composition may take place on the root portion of the hair. The application to the root portion of the hair may still be over the entire head of the end user, but application of the hair colorant composition is applied only to the section of hair closest to the head (root portion), which is between 0.01 mm to 4 mm from the scalp of the head. Also, application may take place on a portion of hair. Application of a portion of hair is commonly referred to as highlighting or lowlighting. The portion of hair may be physically separated from the whole head of hair in a hair bundle or may be a smaller portion of hair than the whole head of hair. A hair bundle may be physically separated from a whole head of hair by a device including a plastic cap through which hair bundles are formed when hair is pulled through orifices in the plastic cap, metal foils encompassing a hair bundle, strand separators applied to hair at the root portion, or similar devices.

When present, an optional conditioning agent can be provided in a third container. In the latter case, all three compositions can be mixed immediately before use and applied together, or the content of the third container can be applied (after an optional rinse step) as a post-treatment immediately after the hair dyeing composition.

According to one method for oxidatively dyeing hair, the method comprises mixing a tint composition and an oxidizing composition together to form a hair dyeing composition, applying a hair dyeing composition to the hair, waiting for a period of 5-45 minutes, such as 20-30 minutes, and then removing the hair dyeing composition from the hair.

The methods of dyeing hair also may further comprise working the hair dyeing composition into the hair by hand or by a tool for a few minutes to ensure uniform application to all of the hair. The hair dyeing composition remains on the hair while the end hair color develops for a time period of 5 to 45 minutes. The consumer then rinses his/her hair thoroughly with tap water and allows it to dry and/or styles the hair.

Kits comprising one container for the first composition (tint composition) and one container for the second composition (oxidizing composition) can be advantageously used for this method. Optionally, a third composition may comprise an alkaline agent, such as monoethanolamine (MEA). The kit further comprises instructions for mixing and application of the hair dyeing composition. The kit may further include an object such as a mixing bowl, an application device, a dispensing device, gloves, hair strand separators, and any combination of these objects. The kit also may comprise an additional container for a composition comprising a conditioning agent.

The hair dyeing compositions may be used in a variety of packaging and dispensing devices. These dispensing devices can come in the form of separate devices that may be used independently or in combination with one another. Typically, the hair colorant compositions are contained within separate single-compartment or multi-compartment containers such that the tint composition and oxidizing composition can be stored separately from one another before use. The tint composition and the oxidizing composition are mixed together in a mixing bowl or in a dispensing device (such as a squeeze bottle, a squeeze foamer, pump foamer, and the like) and then applied to the consumer's hair via a tool (brush, comb, or the like) or by hand after being dispensed from the dispensing device.

Another packaging device involves storing the oxidizing components and tint components, along with any additional ingredients which include but are not limited to surfactants, antioxidants, stabilizers, chelants, thickening agents, and/or polymers, in a bottle or sachet, provided that the ingredients are in powdered form and anhydrous, wherein the hair coloring composition becomes activated by the addition of the prescribed amount of water.

The most common packaging device involves storing the oxidizing composition in a container such as a bottle, tube, squeeze foamer, pump foamer or a sachet and separately storing the tint composition in an additional package such as a bottle, tube or sachet.

EXAMPLES

The following are examples of the syntheses of various dye compounds as described herein.

Example A: Synthesis of 3-chloro-1-methyl-1H-indol-4-aminium chloride

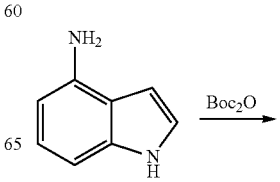

-continued

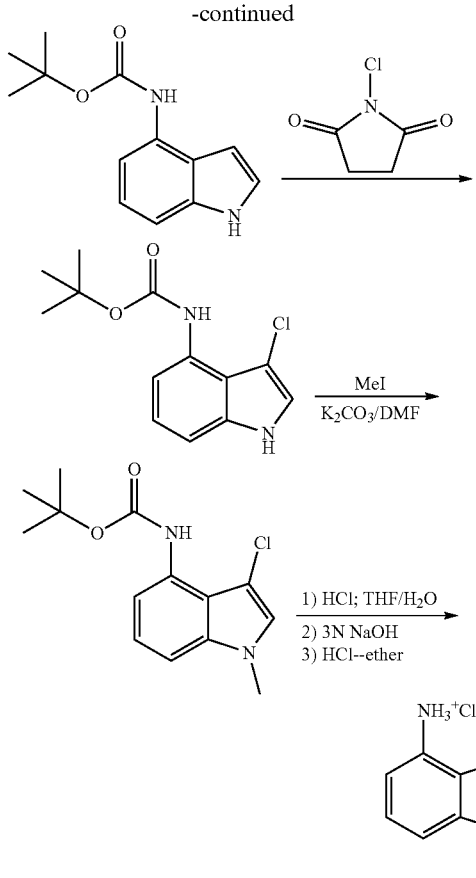

Example B: Synthesis of
3-chloro-n-methyl-1H-indol-4-amine

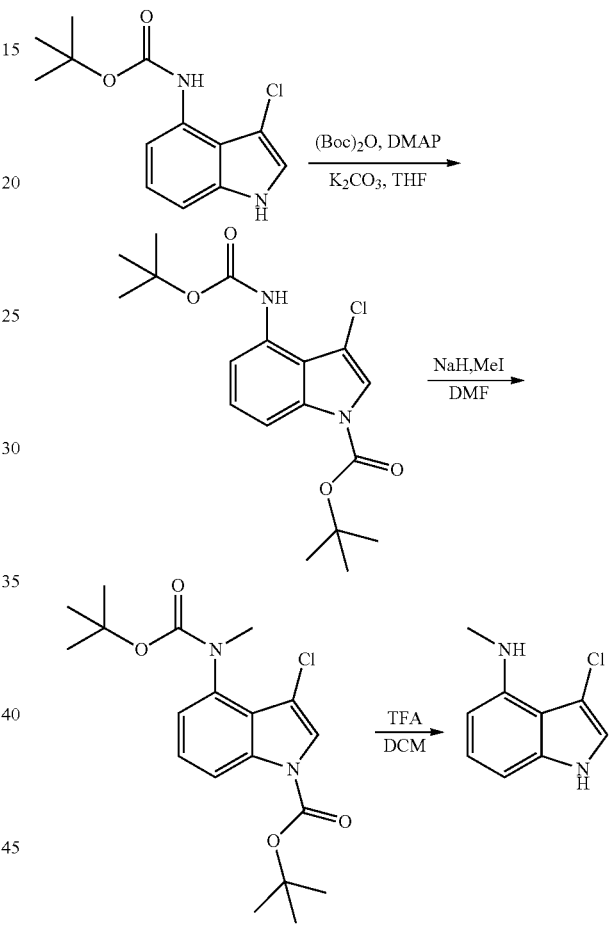

Step 1—Di-t-butyl dicarbonate (9.9 g) is added 1H-indol-4-amine (5 g) in dichloromethane (50 mL). The reaction mixture is stirred at 23° C. for 16 hours, washed with water, and then brine, dried over MgSO₄ and evaporated to dryness. The residue is purified by chromatography on silica gel to yield tert-butyl (1H-indol-4-yl)carbamate as a gray solid (8.34 g).

Step 2—N-Chlorosuccinimide (5.03 g) is added portionwise to a solution of the (1H-indol-4-yl)-carbamic acid t-butyl ester (8.34 g) in tetrahydrofuran (50 mL) in an ice-bath. The reaction mixture is stirred at 23° C. for 18 hours, diluted with ethyl acetate, washed with saturated sodium carbonate, water, and brine, dried over MgSO₄, and evaporated. The residue is purified by chromatography on silica gel to yield tert-butyl (3-chloro-1H-indol-4-yl)carbamate as a white crystalline compound (8.6 g).

Step 3—tert-Butyl (3-chloro-1H-indol-4-yl)carbamate (2 g), potassium carbonate (2.6 g), iodomethane (1.16 g), and dimethylformamide (5 mL) are stirred in a stoppered flask at room temperature for 46 hours. The crude mixture is partitioned between dichloromethane and water. The resulting aqueous layer is extracted with dichloromethane. The combined organic extracts are washed with water and then brine. The organic solution is dried over MgSO₄, filtered, and chromatographed on silica gel. Removal of the solvent yielded the tert-butyl (3-chloro-1-methyl-1H-indol-4-yl)carbamate was 1.85 g (88%).

Step 4—tert-Butyl(3-chloro-1-methyl-1H-indol-4-yl)carbamate (1.82 g) is dissolved in 28 mL of THF. Concentrated HCl (5.6 mL) is added with stirring, and the reaction is stirred at ambient temperature for 65.5 hours. The reaction is quenched with 3N NaOH, and then extracted with ethyl acetate. The combined organic extracts are washed with water, and then brine. The organics are then dried over MgSO₄, filtered, concentrated, and chromatographed on silica gel. After concentration, THF is added to the residue, and the ethyl acetate removed. 3-Chloro-1-methyl-1H-indol-4-aminium chloride is precipitated with HCl and collected by filtration and dried yielding 0.86 g.

Step 1—A mixture of tert-butyl (3-chloro-1H-indol-4-yl)carbamate (300 mg), THF (10 mL), di-t-butyl dicarbonate (368 mg), potassium carbonate (0.5 g) and N,N-dimethylpyridin-4-amine (14 mg, 0.11 mmol). is stirred at room temperature for 16 hours, filtered, and evaporated to dryness. The residue is purified on silica gel to yield tert-butyl 4-((tert-butoxycarbonyl)amino)-3-chloro-1H-indole-1-carboxylate.

Step 2—The tert-butyl 4-((tert-butoxycarbonyl)amino)-3-chloro-1H-indole-1-carboxylate from the previous reaction is combined with dimethylformamide (12 mL) and NaH (60% in mineral oil, 49.5 mg) and stirred at ambient temperature for 30 minutes, then iodomethane (78 μL) is added. The reaction is stirred at ambient temperature for an additional 4 hours and a small piece of dry ice is added. The mixture is partitioned between ethyl acetate and water. The organic layer is washed with water, then brine. The organic solution is dried over MgSO₄ and then concentrated. The residue is purified by silica gel chromatography to yield tert-butyl 4-((tert-butoxycarbonyl) (methyl)amino)-3-chloro-1H-indole-1-carboxylate.

Step 3—A mixture of tert-butyl 4-((tert-butoxycarbonyl)(methyl)amino)-3-chloro-1H-indole-1-carboxylate, dichloromethane (5 mL), and trifluoroacetic acid (1.0 mL, 13 mmol) is stirred overnight. Ammonium hydroxide (5 mL) is added to the reaction mixture, then the solution is concentrated and purified on silica gel. The yield of 3-chloro-N-methyl-1H-indol-4-amine is 46 mg over the three steps.

Example C: Synthesis 3-chloro-1-(2-hydroxyethyl)-1H-indol-4-aminium chloride

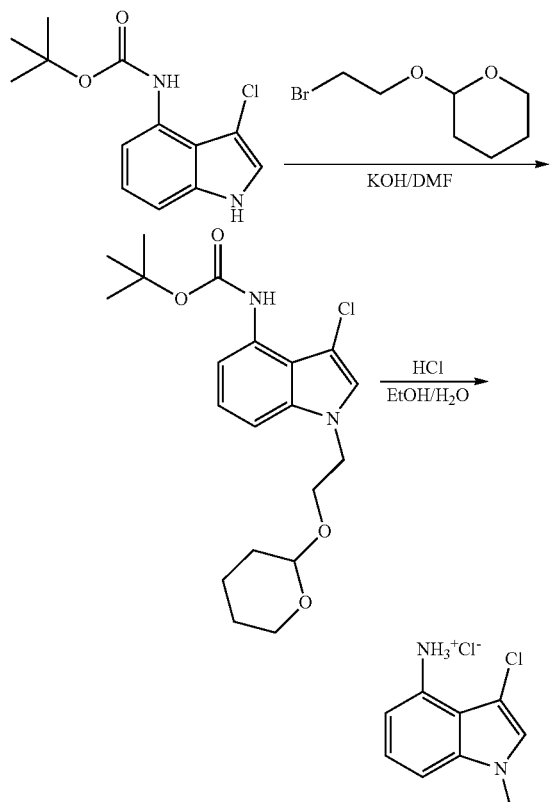

Step 1—tert-Butyl (3-chloro-1H-indol-4-yl)carbamate is dissolved (10 g) and dimethylformamide (30 mL) and KOH (2.3 g), and then 2-(2-bromoethoxy)tetrahydro-2H-pyran (8.6 g) are added, and the mixture is stirred at ambient temperature overnight. The mixture is concentrated and purified on silica gel yielding tert-butyl (3-chloro-1-(2-((tetrahydro-2H-pyran-2-yl)oxy)ethyl)-1H-indol-4-yl)carbamate (12.5 g).

Step 2—tert-Butyl (3-chloro-1-(2-((tetrahydro-2H-pyran-2-yl)oxy)ethyl)-1H-indol-4-yl)carbamate (12.5 g) is dissolved in ethanol (100 mL). Concentrated HCl (15 mL) is added cautiously. The reaction is stirred overnight at ambient temperature, and then evaporated to dryness. The solid is suspended in ethanol, filtered, and rinsed with ethanol yielding 6.8 g of 3-chloro-1-(2-hydroxyethyl)-1H-indol-4-aminium chloride.

Example D: Synthesis of 3-chloro-N,1-dimethyl-1H-indol-4-Amine

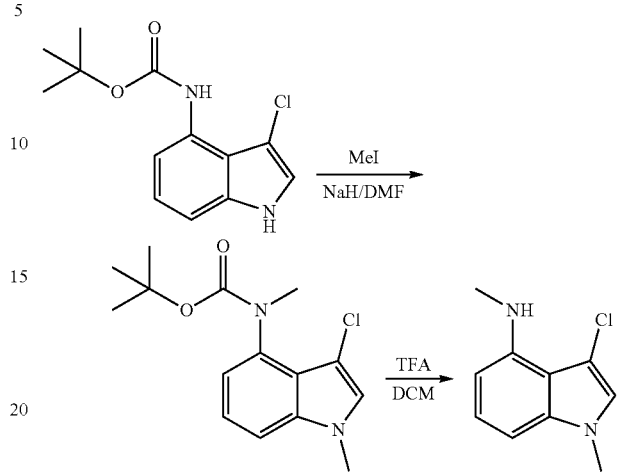

Step 1—tert-Butyl (3-chloro-1H-indol-4-yl)carbamate (300 mg), DMF (4 mL) and NaH (60% in mineral oil; 100 mg) is stirred at room temperature for 30 minutes. Iodomethane (156 □L) is added. The reaction mixture is stirred at ambient temperature for an additional 8 hours and a small piece of dry ice is added. The mixture is partitioned between ethyl acetate and water. The organic layer is washed with water, brine, dried over MgSO$_4$, and concentrated under reduced pressure. The residue is purified on silica gel to yield tert-butyl (3-chloro-1-methyl-1H-indol-4-yl)(methyl)carbamate.

Step 2—Trifluoroacetic acid (10 mL) is added to a solution of tert-butyl (3-chloro-1-methyl-1H-indol-4-yl)(methyl)carbamate from the previous step. The mixture is stirred overnight and the reaction is quenched with ammonium hydroxide (10 mL). The solution is evaporated to dryness and purified on silica gel to yield 200 mg of 3-chloro-N,1-dimethyl-1H-indol-4-amine as a white crystalline material in 91% overall yield for the two steps.

Example E: Synthesis of 3-chloro-1-ethyl-1H-indol-4-aminium chloride

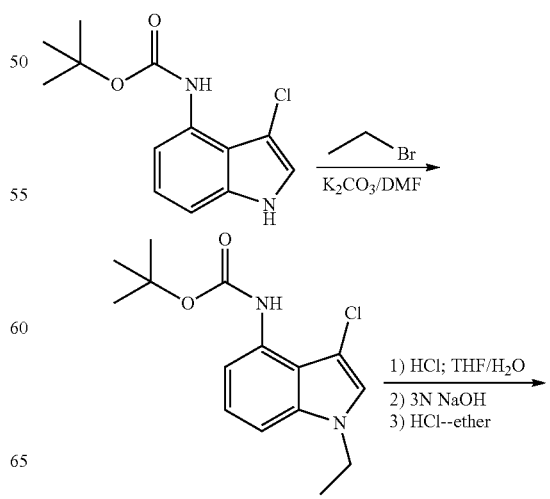

-continued

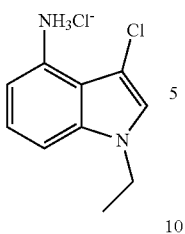

Step 1—A mixture of tert-butyl (3-chloro-1H-indol-4-yl)carbamate (2 g), potassium carbonate (2.6 g), DMF (5 mL), and bromoethane (0.92 g) is stirred for 64 hours at ambient temperature. The crude mixture is partitioned between dichloromethane and water. The aqueous layer is extracted with dichloromethane. The combined organic extracts are washed with water, then brine. The organic solution is dried over magnesium sulfate, filtered, and chromatographed on silica gel. The pure fractions are combined, and the solvent removed, to give 1.95 g of tert-butyl (3-chloro-1-ethyl-1H-indol-4-yl)carbamate.

Step 2—tert-Butyl (3-chloro-1-ethyl-1H-indol-4-yl)carbamate (1.95 g), tetrahydrofuran (28 mL), and concentrated HCl (5.6 mL) are combined, stoppered round bottom flask and stirred at ambient temperature for 18 hours. The reaction is quenched with 3N NaOH (200 mL). The mixture is extracted with ethyl acetate, washed with water, brine, and the organic fraction is dried over magnesium sulfate then filtered and chromatographed on silica. After evaporation of the ethyl acetate, the residue is added to 2 M HCl in diethyl ether (2 5 mL) and tetrahydrofuran (25 mL). The resulting slurry is stirred for 30 minutes, filtered, rinsed with tetrahydrofuran, and dried to give 0.97 g of 3-chloro-1-ethyl-1H-indol-4-aminium chloride.

Example F: Synthesis of 1-amino-3-(4-amino-3-chloro-1H-indol-1-yl)propan-2-ol

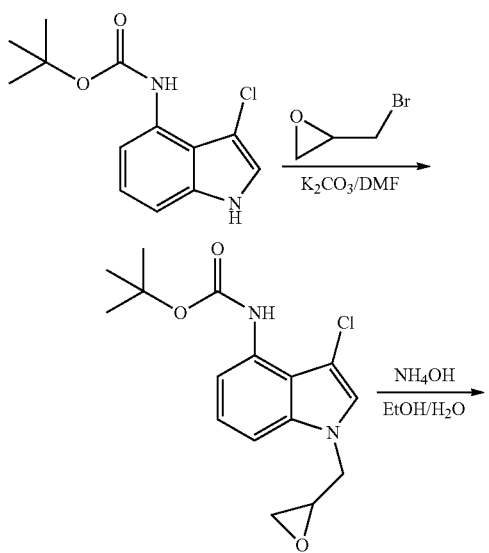

-continued

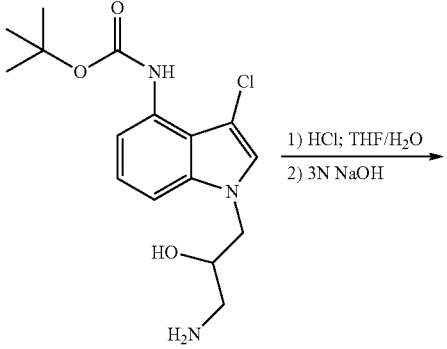

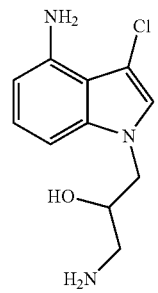

Step 1—A solution of 2.87 g of 2-(bromomethyl)oxirane in 15 mL of DMF is added to 5 g of tert-butyl (3-chloro-1H-indol-4-yl)carbamate and 6.49 g of $K_2CO_3$ is added, and the reaction is stirred at ambient temperature for 16 hours. The mixture is partitioned between dichloromethane and water. The aqueous layer is extracted with dichloromethane, and the combined organic extracts are washed with water, then brine. The organic solution is dried over magnesium sulfate, filtered, and chromatographed on silica. The pure fractions are combined, the solvent is removed, and the solid is dried, yielding 3.05 g of tert-butyl (3-chloro-1-(oxiran-2-ylmethyl)-1H-indol-4-yl)carbamate.

Step 2—tert-Butyl(3-chloro-1-(oxiran-2-ylmethyl)-1H-indol-4-yl)carbamate (2.20 g), 50 mL of ethanol, and 25 mL of 28% ammonium hydroxide are stirred at ambient temperature for 23 hours. The reaction mixture is concentrated and chromatographed on silica gel. The pure fractions were combined and the solvent was removed, giving 1.92 g of tert-butyl (1-(3-amino-2-hydroxypropyl)-3-chloro-1H-indol-4-yl)carbamate.

Step 3—tert-Butyl (1-(3-amino-2-hydroxypropyl)-3-chloro-1H-indol-4-yl)carbamate (1.92), 17 mL of THF, and 3.4 mL of concentrated HCl are stirred at ambient temperature until the reaction is complete. The reaction is quenched with 200 mL of 3N NaOH, and extracted with ethyl acetate. The combined organic extracts are washed with brine. The organic solution is dried over magnesium sulfate, filtered, concentrated, and chromatographed on silica. Solvent is removed from the pure fractions, and the solid is dried in vacuo to give 0.52 g of 1-amino-3-(4-amino-3-chloro-1H-indol-1-yl)propan-2-ol.

Example G: Synthesis of 1-(2-aminoethyl)-3-chloro-1H-indol-4-amine

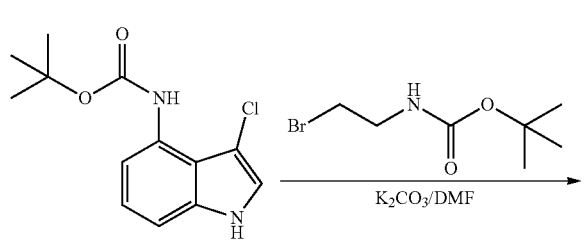

Example H: Synthesis of 1-(3-aminopropyl)-3-chloro-1H-indol-4-amine

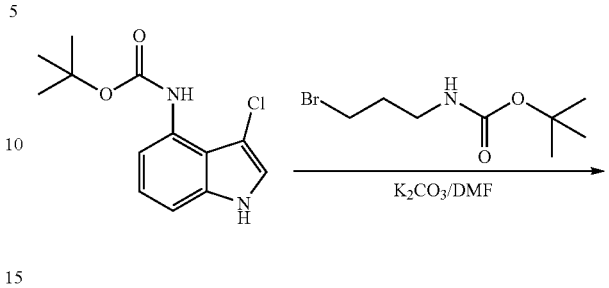

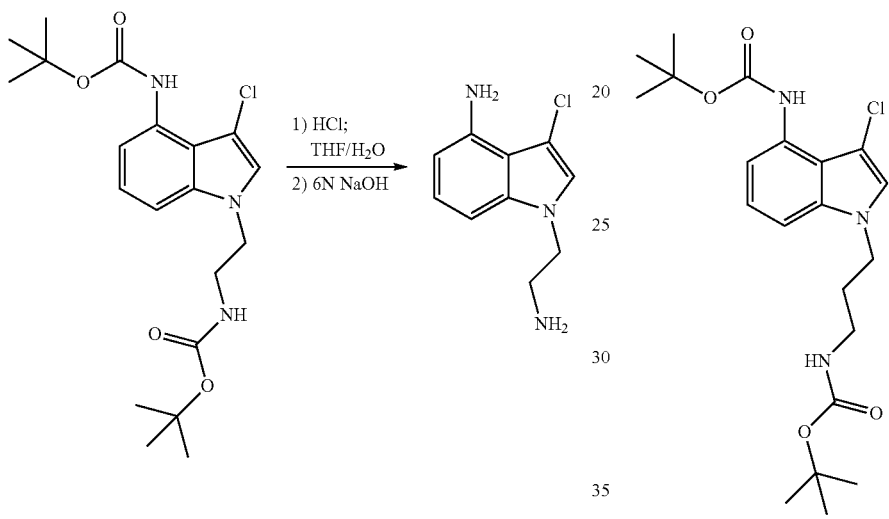

Step 1—tert-Butyl (3-chloro-1H-indol-4-yl)carbamate (2.5 g), dimethylformamide (7.5 mL), tert-butyl (2-bromoethyl)carbamate (2.31 g), and potassium carbonate (2.6 g) are stirred at ambient temperature. After 18.5 hours, additional tert-butyl(2-bromoethyl)carbamate (3.17 g) and potassium carbonate (4.46 g) are added. The reaction is stirred at ambient temperature for 73 hours. The mixture is partitioned between dichloromethane and water. The aqueous layer is extracted with dichloromethane, and the combined organic extracts are washed with water, then brine. The organic solution is dried over magnesium sulfate, filtered, and chromatographed on silica. The pure fractions are combined, the solvent is removed, and the product is dried, yielding 2.61 g of tert-butyl (1-(2-((tert-butoxycarbonyl)amino)ethyl)-3-chloro-1H-indol-4-yl)carbamate.

Step 2—tert-Butyl (1-(2-((tert-butoxycarbonyl)amino)ethyl)-3-chloro-1H-indol-4-yl)carbamate (2.61 g) is dissolved in 27 mL of THF and concentrated HCl (5.3 mL) is added slowly. The flask is stoppered and the reaction is stirred until complete. The reaction is quenched with 6N NaOH (100 mL), and the mixture is extracted with ethyl acetate, washed with water, and then brine. The organic solution is dried over magnesium sulfate, filtered, concentrated, and chromatographed on silica. The pure fractions are combined and the solvent is removed to give 0.6 g of 1-(2-aminoethyl)-3-chloro-1H-indol-4-amine.

Step 1—tert-Butyl (3-chloro-1H-indol-4-yl)carbamate (1 g), dimethylformamide (3 mL), tert-butyl (2-bromopropyl)carbamate (0.98 g), and potassium carbonate (1.3 g) are stirred at ambient temperature. The reaction is stirred at ambient temperature for 17 hours. The mixture is partitioned between dichloromethane and water. The aqueous layer is extracted with dichloromethane, and the combined organic extracts are washed with water, then brine. The organic solution is dried over magnesium sulfate, filtered, concentrated, and chromatographed on silica. The pure fractions are combined, the solvent is removed, and the product is dried, yielding 1.13 g of tert-butyl (1-(3-((tert-butoxycarbonyl)amino)propyl)-3-chloro-1H-indol-4-yl)carbamate.

Step 2—tert-Butyl(1-(3-((tert-butoxycarbonyl)amino)propyl)-3-chloro-1H-indol-4-yl)carbamate (0.98 g) is dissolved in 10 mL of THF, and concentrated HCl (5.3 mL) is added slowly. The flask is stoppered and the reaction is stirred for 4 days. The reaction is quenched with 6N NaOH (100 mL), and the mixture is extracted with ethyl acetate, washed with water, and then brine. The organic solution is treated with methanolic triethylamine, dried over magnesium sulfate, filtered, concentrated, and chromatographed on silica. The pure fractions are combined and the solvent is removed to give 0.22 g of 1-(2-aminopropyl)-3-chloro-1H-indol-4-amine.

Example I: Synthesis of 3-chloro-1-propyl-1H-indol-4-aminium chloride

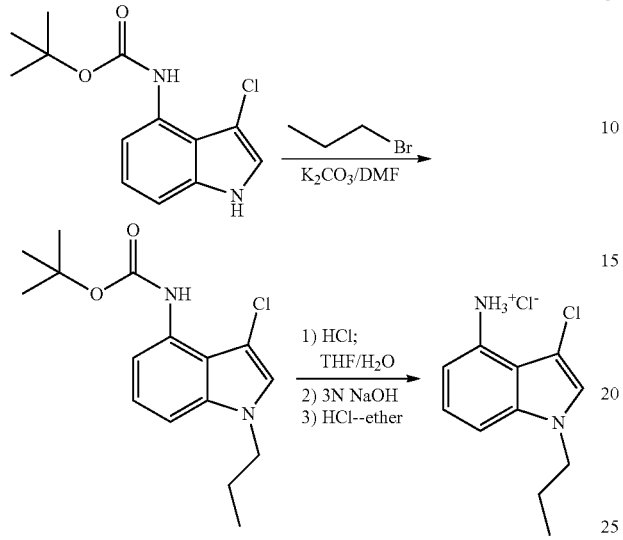

Step 1—tert-Butyl (3-chloro-1H-indol-4-yl)carbamate (2 g), dimethylformamide (5 mL), 1-bromopropane (1.02 g), and potassium carbonate (2.6 g) are stirred under nitrogen at ambient temperature for 19 hours. The mixture is partitioned between dichloromethane and water. The aqueous layer is extracted with dichloromethane, and the combined organic extracts are washed with water, then brine. The organic solution is dried over magnesium sulfate, filtered, and chromatographed on silica. The pure fractions are combined, concentrated, and dried, yielding 2 g of tert-butyl (3-chloro-1-propyl-1H-indol-4-yl)carbamate.

Step 2—tert-Butyl(3-chloro-1-propyl-1H-indol-4-yl)carbamate (1.98 g) was dissolved in 28 mL of THF and concentrated HCl (5.6 mL) is added slowly. The flask is stoppered and the reaction is stirred at ambient temperature for 43.5 hours. The reaction is quenched with 3N NaOH (200 mL), and the mixture was extracted with ethyl acetate, washed with water, and then brine. The organic solution is dried over magnesium sulfate, filtered, and chromatographed on silica. The pure fractions are combined and concentrated. 25 mL of 2 M HCl in diethyl ether and tetrahydrofuran (25 mL) is added to the residue and the resulting slurry is stirred for 30 minutes. The solid is filtered and rinsed with tetrahydrofuran. The resulting solid is treated with methanol, suspended in tetrahydrofuran, and filtered to give 1.06 g of 3-chloro-1-propyl-1H-indol-4-aminium chloride.

Example J: Synthesis of 3-chloro-1-butyl-1H-indol-4-aminium chloride

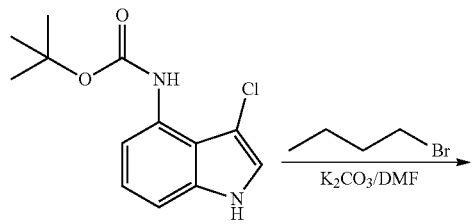

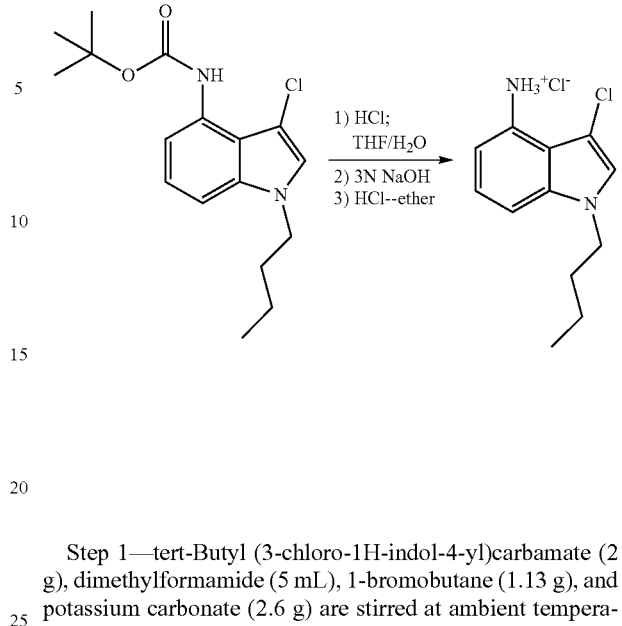

Step 1—tert-Butyl (3-chloro-1H-indol-4-yl)carbamate (2 g), dimethylformamide (5 mL), 1-bromobutane (1.13 g), and potassium carbonate (2.6 g) are stirred at ambient temperature for 48 hours. The mixture is partitioned between dichloromethane and water. The aqueous layer is extracted with dichloromethane, and the combined organic extracts are washed with water, then brine. The organic solution is dried over magnesium sulfate, filtered, and chromatographed on silica. The pure fractions are combined, concentrated, and dried, yielding 2.03 g of tert-butyl (1-butyl-3-chloro-1H-indol-4-yl)carbamate Step 2—tert-Butyl(1-butyl-3-chloro-1H-indol-4-yl)carbamate (2 g), tetrahydrofuran (28.0 mL), is dissolved in 28 mL of THF and concentrated HCl (5.6 mL) is added slowly. The flask is stoppered and the reaction is stirred at ambient temperature for 97 hours. The reaction is quenched with 3N NaOH (200 mL), and the mixture is extracted with ethyl acetate, washed with water, and then brine. The organic solution is dried over magnesium sulfate, filtered, and chromatographed on silica. The pure fractions were combined and concentrated, and chromatographed on silica a second time. The pure fractions were combined and concentrated yielding a purple oil. The oil was dissolved in tetrahydrofuran, and then 2 M HCl in diethyl ether (25 mL) is added. The resulting white precipitate is stirred for 30 minutes at room temperature, filtered, rinsed with tetrahydrofuran, and dried giving 0.5 g of 3-chloro-1-butyl-1H-indol-4-aminium chloride.

Example K: Synthesis of 3-Chloro-1-Hexyl-1H-Indol-4-Aminium Chloride

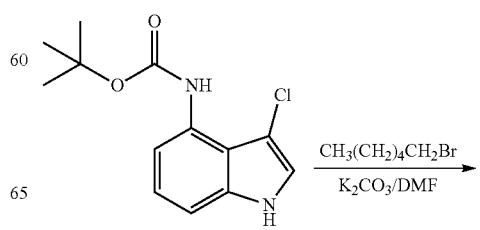

-continued

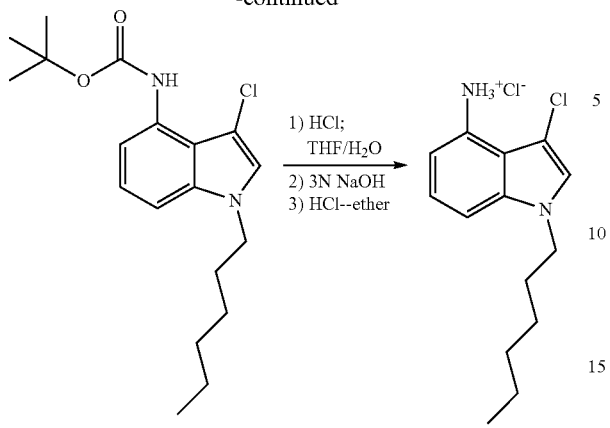

1) HCl; THF/H₂O
2) 3N NaOH
3) HCl--ether

Step 1—tert-Butyl (3-chloro-1H-indol-4-yl)carbamate (2 g), dimethylformamide (5 mL), 1-bromohexane (1.38 g), and potassium carbonate (2.6 g) are stirred at ambient temperature for 48 hours. The mixture is partitioned between dichloromethane and water. The aqueous layer is extracted with dichloromethane, and the combined organic extracts are washed with water, then brine. The organic solution is dried over magnesium sulfate, filtered, and chromatographed on silica. The pure fractions are combined, the solvent is removed, and the solid is dried, yielding 2.27 g of tert-butyl (3-chloro-1-hexyl-1H-indol-4-yl)carbamate.

Step 2—tert-Butyl(1-hexyl-3-chloro-1H-indol-4-yl)carbamate (2.26 g) is dissolved in 28 mL of THF and concentrated HCl (5.6 mL) is added slowly. The flask is stoppered and the reaction is stirred at ambient temperature for 97 hours. The reaction is quenched with 3N NaOH (200 mL), and the mixture is extracted with ethyl acetate, washed with water, and then brine. The organic solution is dried over magnesium sulfate, filtered, concentrated, and chromatographed on silica. The pure fractions were combined and concentrated, and chromatographed on silica a second time. The pure fractions are combined and concentrated. The oil is dissolved in 1:1 THF:methanol, and then 2 M HCl in diethyl ether (25 mL) was added. The resulting solid is taken up in tetrahydrofuran (40 mL) and sonicated then stirred. The solid was filtered, rinsed with tetrahydrofuran, and dried, yielding 0.73 g of 3-chloro-1-hexyl-1H-indol-4-aminium chloride.

Example L: Synthesis of 3-chloro-1-(2-methoxyethyl)-1H-indol-4-aminium chloride

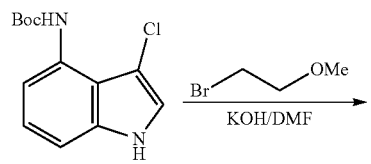

KOH/DMF

-continued

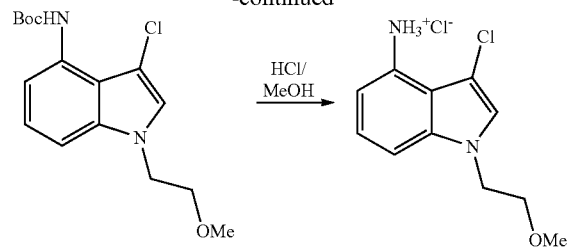

HCl/MeOH

Step 1—tert-Butyl (3-chloro-1H-indol-4-yl)carbamate (10 g) is dissolved in DMF (30 mL). Potassium hydroxide (2.31 g, 41.3 mmol, 1.1 eq.) and 1-bromo-2-methoxyethane (5.73 g) are added to the solution sequentially. The reaction mixture is stirred overnight at ambient temperature, and then purified on silica gel to yield 10.7 g of tert-butyl (3-chloro-1-(2-methoxyethyl)-1H-indol-4-yl)carbamate.

Example M: Synthesis of 3-chloro-N,1-bis(2-hydroxyethyl)-1H-indol-4-aminium chloride Step 1—tert-Butyl (3-chloro-1H-indol-4-yl)carbamate (5 g) is dissolved in DMF (20 mL), and the solution is cooled in ice-water bath. Sodium hydride (60% dispersion in mineral oil, 1.65 g) is added to the solution in portions and stirred at 0-5° C. for 20 minutes until the evolution of gas could no longer be observed. 2-(2-Bromoethoxy)tetrahydro-2H-pyran (8.62) is then added to the solution dropwise. The reaction mixture is stirred overnight at ambient temperature then purified on silica gel to yield tert-butyl 6.57 g of tert-butyl (3-chloro-1-(2-((tetrahydro-2H-pyran-2-yl)oxy)ethyl)-1H-indol-4-yl)(2-((tetrahydro-2H-pyran-2-yl)oxy)ethyl)carbamate.

Step 2—tert-Butyl (3-chloro-1-(2-((tetrahydro-2H-pyran-2-yl)oxy)ethyl)-1H-indol-4-yl)(2-((tetrahydro-2H-pyran-2-yl)oxy)ethyl)carbamate (4 g) is dissolved in methanolic HCl (3 N, 20 mL) and stirred at room temperature for 2 hours. The mixture is evaporated in vacuo to produce 1.91 g of 3-chloro-N,1-bis(2-hydroxyethyl)-1H-indol-4-aminium chloride.

Example N: Synthesis of 1,1'-(propane-1,3-diyl)bis(3-chloro-1H-indol-4-aminium) chloride

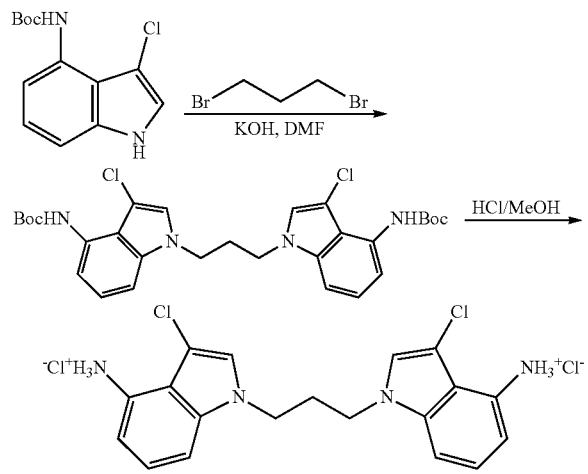

Step 1—tert-Butyl (3-chloro-1H-indol-4-yl)carbamate (10 g) is dissolved in DMF (40 mL). Potassium hydroxide (2.31 g) and 1,3-dibromopropane (3.78 g) are then added to the solution sequentially. The reaction mixture is stirred overnight at ambient temperature, then purified on silica gel to yield 7.42 g of di-tert-butyl (propane-1,3-diylbis(3-chloro-1H-indole-1,4-diyl))dicarbamate.

Step 2—Di-tert-butyl (propane-1,3-diylbis(3-chloro-1H-indole-1,4-diyl))dicarbamate (5 g) is dissolved in methanolic HCl (3 N, 20 mL) and stirred at room temperature for 2 hours. The mixture is evaporated in vacuo to produce 3.81 g of 1,1'-(propane-1,3-diyl)bis(3-chloro-1H-indol-4-aminium) chloride.

The following are examples of the dye compositions comprising the novel compounds of the present invention.

Exemplary Dye Formulations

| | % by weight |
|---|---|
| Composition A | |
| 3-chloro-1H-indol-4-amine derivative[1] | 0.005-5.0 |
| Primary Intermediate[5] | 0.005-5.0 |
| Ammonium Hydroxide (aq. 28% active) | 4.50 |
| Water | q.s. to 100 |
| Composition B | |
| 3-chloro-1H-indol-4-amine derivative[1] | 0.005-5.0 |
| Primary Intermediate[5] | 0.005-5.0 |
| Ammonium carbonate | 10.00 |
| Water | q.s. to 100 |
| Composition C | |
| 3-chloro-1H-indol-4-amine derivative[1] | 0.005-5.0 |
| Primary Intermediate[5] | 0.005-5.0 |
| FlexiThix ™[3] | 5.00 |
| Phenoxyethanol | 0.30 |
| Sodium Benzoate | 0.30 |
| Disodium EDTA | 0.10 |
| Ammonium Hydroxide (aq. 28% active) | 4.00 |
| Water | q.s. to 100 |
| Composition D | |
| 3-chloro-1H-indol-4-amine derivative[1] | 0.005-5.0 |
| Primary Intermediate[5] | 0.005-5.0 |
| Aculyn ™ 46[4] | 15.80 |
| Phenoxyethanol | 0.30 |
| Sodium Benzoate | 0.30 |
| Disodium EDTA | 0.10 |
| Ammonium Hydroxide (aq. 28% active) | 4.00 |
| Water | q.s. to 100 |
| Composition E | |
| 3-chloro-1H-indol-4-amine derivative[1] | 0.005-5.0 |
| Primary Intermediate[5] | 0.005-5.0 |
| Plantaren ® 2000 N UP[2] | 20.00 |
| Phenoxyethanol | 0.30 |
| Sodium Benzoate | 0.30 |
| Disodium EDTA | 0.10 |
| Ammonium Hydroxide (aq. 28% active) | 4.00 |
| Water | q.s. to 100 |
| Composition F | |
| 3-chloro-1H-indol-4-amine derivative[1] | 0.005-5.0 |
| Primary Intermediate[5] | 0.005-5.0 |
| Non-anionic foaming agent | 5.00 |
| Phenoxyethanol | 0.30 |
| Sodium Benzoate | 0.30 |
| Disodium EDTA | 0.10 |
| Ammonium Hydroxide (aq. 28% active) | 4.00 |
| Water | q.s. to 100 |
| Composition G | |
| 3-chloro-1H-indol-4-amine derivative[1] | 0.005-5.0 |
| Primary Intermediate[5] | 0.005-5.0 |
| Lanolin alcohol | 2.00 |
| Stearate mix | 5.5 |
| Glycol Distearate | 2.0 |
| Cetearyl alcohol and SLS (90:10 mix) | 17.5 |
| Sodium cocoyl isethionate | 0.46 |
| Sodium laureth sulfate | 4.0 |
| Ascorbic acid | 0.3 |
| Sodium sulfate | 0.001 |
| Sodium sulfite | 0.4 |
| Disodium EDTA | 0.1 |
| Fragrance | 0.25 |
| Ammonium Hydroxide (aq. 28% active) | 4.00 |
| Water | q.s. to 100 |
| Composition H | |
| 3-chloro-1H-indol-4-amine derivative[1] | 0.005-5.0 |
| Primary Intermediate[5] | 0.005-5.0 |
| Sodium sulfite | 0.10 |
| Erythorbic Acid | 0.40 |
| Ethanol | 31.5 |
| Ammonium Hydroxide (aq. 28% active) | 4.00 |
| Water | q.s. to 100 |

[1]The 3-halo-1H-indol-4-amine derivative may be any one of the compounds described herein
[2](chemical makeup supplied by BASF)
[3]PVP polymer supplied by Ashland
[4]PEG-150/Stearyl/SMDI copolymer supplied by Rohm and Haas
[5]The concentration of the primary intermediate is dependent upon the concentration of the 3-halo-1H-indol-4-amine derivative according to the present invention, and is approximately equimolar.

What is claimed is:

1. A 3-halo-1H-indol-4-amine compound of general formula (I)

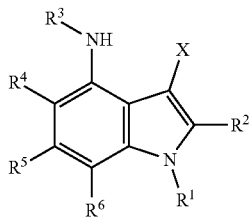

wherein radical X is a halogen atom selected from the group consisting of chlorine or bromine;
wherein radicals $R^1$ and $R^3$ are the same or different and are selected from the group consisting of:
  (a) N-linked monovalent substituents selected from the group consisting of:
    (i) substituted or unsubstituted, straight or branched, alkyl, mono- or poly-unsaturated alkyl, heteroalkyl, aliphatic, heteroaliphatic, or heteroolefinic systems;
    (ii) substituted or unsubstituted, mono- or polycyclic aliphatic;
    (iii) an aromatic ring or 5- or 6-membered heteroaromatic rings having at least one nitrogen, oxygen or sulfur atom; and,
    (iv) substituted or unsubstituted, mono- or polyhydroxy-, mono- or polyamino-, mono- or polyfluoro-alkyl systems, or mixtures thereof; wherein said systems of (i) and (ii) comprise from about 1 to about 10 carbon atoms and from about 0 to about 5 heteroatoms selected from the group consisting of O, S, N, P, and Si;
  (b) hydrogen;
  (c) a linker group (L) between one of the radical $R^1$ or $R^3$ of a first compound of formula (I) and between one of the radical $R^1$ or $R^3$ of a second compound of formula (I), both compounds forming therefore a dimeric structure, wherein the linker group is of general formula (L)

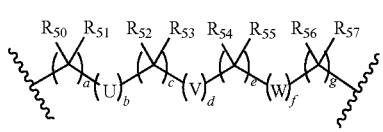

wherein
  (i) a, c, e and g are each independently an integer from 0 to 3, provided that the sum of a, c, e and g is greater than or equal to 2; b, d and f are each independently 0 or 1; and $R_{50}$, $R_{51}$, $R_{52}$, $R_{53}$, $R_{54}$, $R_{55}$, $R_{56}$ and $R_{57}$ are each independently hydrogen or $C_1$-$C_2$ alkyl group;
  (ii) U is an aromatic ring, alkenyl or alkynyl moiety;
  (iii) V is O, N or S; and
  (iv) W is a cyclic aliphatic ring;
wherein radicals $R^2$ and $R^5$ are the same or different and are selected from the group consisting of:
  (a) C-linked monovalent substituents selected from the group consisting of:
    (i) substituted or unsubstituted, straight or branched, alkyl, mono- or poly-unsaturated alkyl, heteroalkyl, aliphatic, heteroaliphatic, or heteroolefinic systems;
    (ii) substituted or unsubstituted, mono- or polycyclic aliphatic;
    (iii) halogen atom;
    (iv) a boronic acid group, a boronic ester group;
    (v) an aromatic ring or 5- or 6-membered heteroaromatic rings having at least one nitrogen, oxygen or sulfur atom; and,
    (vi) substituted or unsubstituted, mono- or polyhydroxy-, mono- or polyamino-, mono- or polyfluoro-alkyl systems, or mixtures thereof; wherein said systems of (i) and (ii) comprise from about 1 to about 10 carbon atoms and from about 0 to about 5 heteroatoms selected from the group consisting of O, S, N, P, and Si;
  (b) S-linked monovalent substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;
  (c) O-linked monovalent substituents selected from the group consisting of $OA^1$, and $ONA^1A^2$;
  (d) N-linked monovalent substituents selected from the group consisting of $NA^1A^2$, $(NA^1A^2A^3)^+$, $NA^1OA^2$, $NA^1SA^2$, $N=NA^1$, $N=NOA^1$, $NA^1CN$, and $NA^1NA^2A^3$;
  (e) monovalent substituents selected from the group consisting of $COOA^1$, $CONA^1_2$, $CONA^1COA^2$, and $C(=NA^1)NA^1A^2$;
  (f) fluoroalkyl monovalent substituents selected from the group consisting of mono-, poly-, and per-fluoro alkyl systems comprising from about 1 to about 12 carbon atoms and from about 0 to about 4 heteroatoms; and
  (g) hydrogen;
wherein $A^1$, $A^2$, and $A^3$ are monovalent and are independently selected from the group consisting of: H; substituted or unsubstituted, straight or branched, alkyl, mono- or poly-unsaturated alkyl, heteroalkyl, aliphatic, heteroaliphatic, or heteroolefinic systems; substituted or unsubstituted, mono- or poly-cyclic aliphatic, aryl, or heterocyclic systems; and substituted or unsubstituted, mono-, poly-, per-fluoro alkyl systems or $A^1$ and $A^2$ together with nitrogen atom to which they are bound form a ring, wherein said systems comprise from about 1 to about 10 carbon atoms and from about 0 to about 5 heteroatoms selected from the group consisting of O, S, N, P, and Si;
wherein one of radicals $R^4$ or $R^6$ is selected from the group consisting of a hydrogen atom and/or a nucleofuge group;
wherein the nucleofuge group is selected from the group consisting of an alkoxy radical, an alkoxyalkyl radical, alkoxycarbonyl radical, an aryloxy group, a heteroaryloxy radical, an aryloxycarbonylamino radical, or an aryloxycarbonyl radical;
wherein the other radical $R^6$ or $R^4$ is selected from the group consisting of:
  (a) C-linked monovalent substituents selected from the group consisting of:
    substituted or unsubstituted, straight or branched, alkyl, mono- or poly-unsaturated alkyl, heteroalkyl, aliphatic, heteroaliphatic, or heteroolefinic systems;
    (ii) substituted or unsubstituted, mono- or polycyclic aliphatic;

(iii) halogen atom;
(iv) a boronic acid group, a boronic ester group;
(v) an aromatic ring or 5- or 6-membered heteroaromatic rings having at least one nitrogen, oxygen or sulfur atom; and,
(vi) substituted or unsubstituted, mono- or polyhydroxy-, mono- or polyamino-, mono- or polyfluoro- alkyl systems, or mixtures thereof; wherein said systems of (i) and (ii) comprise from about 1 to about 10 carbon atoms and from about 0 to about 5 heteroatoms selected from the group consisting of O, S, N, P, and Si;
(b) S-linked monovalent substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;
(c) O-linked monovalent substituents selected from the group consisting of $ONA^1A^2$;
(d) monovalent substituents selected from the group consisting of $COOA^1$, $CONA^1_2$, $CONA^1COA^2$, and $C(=NA^1)NA^1A^2$;
(e) fluoroalkyl monovalent substituents selected from the group consisting of mono-, poly-, and per-fluoro alkyl systems comprising from about 1 to about 12 carbon atoms and from about 0 to about 4 heteroatoms; and
wherein $R^4$ and $R^6$ are not both selected from hydrogen;
(f) hydrogen;
wherein $A^1$, $A^2$, and $A^3$ are monovalent and are independently selected from the group consisting of: H; substituted or unsubstituted, straight or branched, alkyl, mono- or poly-unsaturated alkyl, heteroalkyl, aliphatic, heteroaliphatic, or heteroolefinic systems; substituted or unsubstituted, mono- or poly-cyclic aliphatic, aryl, or heterocyclic systems; and substituted or unsubstituted, mono-, poly-, per-fluoro alkyl systems or $A^1$ and $A^2$ together with nitrogen atom to which they are bound form a ring; wherein said systems comprise from about 1 to about 10 carbon atoms and from about 0 to about 5 heteroatoms selected from the group consisting of O, S, N, P, and Si; and
their salts thereof;
wherein the 3-halo-1H-indol-4-amine compound of formula (1) is not the compound of formula (I.01) or of formula (I.02)

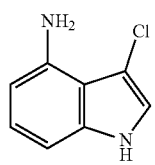

(I.01)

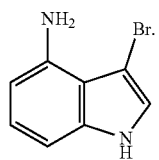

(I.02)

2. The 3-halo-1H-indol-4-amine compound of general formula (I), according to claim 1,
wherein the aromatic ring or 5- or 6-membered heteroaromatic rings having at least one nitrogen oxygen or sulfur atom are, for any one of the radicals $R^1$, $R^2$, $R^3$, $R^4$, $R^5$ and/or $R^6$, selected from the group consisting pyridine, pyrrole, thiophene, furan, imidazole, thiazole, thiadiazole, pyrazole, oxazole, pyrimidine, naphthalene, benzothiazole, indole, benzoxazole, benzimidazole or azulene.

3. The 3-halo-1H-indol-4-amine compound of general formula (I), according to claim 1,
wherein the halogen atom, for any one of the radicals $R^2$, $R^4$, $R^5$ and/or $R^6$, is selected the group consisting of chlorine, bromine, iodine or fluorine.

4. The 3-halo-1H-indol-4-amine compound of general formula (I), according to claim 1,
wherein any one of the radicals $R^1$ and/or $R^3$ is selected from the group consisting of a hydrogen atom, $C_1$-$C_6$ alkyl radical, $C_1$-$C_6$ hydroxyl alkyl radical, $C_1$-$C_6$ polyhydroxy alkyl radical, trifluoromethyl radical, aminoalkyl radical, polyaminoalkyl radical, N-substituted aminoalkyl radical, N,N-disubstituted aminoalkyl radical, acetylamido radical, a carboxyl radical, an alkoxy radical, an alkoxyalkyl radical, a carbamoyl radical, an alkylcarbamoylradical, a hydroxyalkylcarbamoyl radical, an amido radical, an alkylamido radical, an alkylcarbonyl radical, an alkoxycarbonyl radical, an aryloxy radical, an acyloxy radical, an alkylthio radical, an arylthio radical, a heteroarylthio radical, a heteroaryloxy radical, a 5- or 6-membered heterocycle having at least one nitrogen, oxygen or sulfur atom, which is optionally substituted, an aryl radical, which is optionally substituted, a sulfonyl radical, a sulfinyl radical, a phosphonyl radical, a sulfamoyl radical, a siloxy radical, an acyloxy radical, a carbamoyloxy radical, a sulphonamide radical, an imide radical, a ureido radical, a sulfamoylamino radical, an alkoxycarbonylamino radical, an aryloxycarbonylamino radical, an aryloxycarbonyl radical, and a benzenesulfonamido radical.

5. The 3-halo-1H-indol-4-amine compound of general formula (I), according to claim 1,
wherein radical $R^2$ is selected from the group consisting of a hydrogen atom, a halogen atom, a $C_1$-$C_6$ alkyl radical, a $C_1$-$C_6$ hydroxyl alkyl radical, a $C_1$-$C_6$ polyhydroxy alkyl radical, a trifluoromethyl radical, an alkylamino radical, a hydroxyalkylamino radical, an acetylamido radical, a carboxyl radical, an alkoxy radical, an alkoxyalkyl radical, a carbamoyl radical, an alkylcarbamoylradical, a hydroxyalkylcarbamoyl radical, an amido radical, an alkylamido radical, an alkylcarbonyl radical, an alkoxycarbonyl radical, an aryloxy radical, an acyloxy radical, an alkylthio radical, an arylthio radical, a heteroarylthio radical, a heteroaryloxy radical, a 5- or 6-membered heterocycle having at least one nitrogen, oxygen or sulfur atom, which is optionally substituted, an aryl radical, which is optionally substituted, a sulfonyl radical, a sulfinyl radical, a phosphonyl radical, a sulfamoyl radical, a siloxy radical, an acyloxy radical, a carbamoyloxy radical, a sulphonamide radical, an imide radical, an ureido radical, a sulfamoylamino radical, an alkoxycarbonylamino radical, an aryloxycarbonylamino radical, an aryloxycarbonyl radical, and a benzenesulfonamido radical.

6. The 3-halo-1H-indol-4-amine compound of general formula (I), according to claim 1,
wherein the radical $R^5$ is selected from the group consisting of a hydrogen atom, a halogen atom, an amino radical, a hydroxyl radical, a $C_1$-$C_6$ alkyl radical, a $C_1$-$C_6$ hydroxyl alkyl radical, a $C_1$-$C_6$ polyhydroxy alkyl radical, a trifluoromethyl radical, an alkylamino radical, a hydroxyalkylamino radical, an acetylamido radical, a carboxyl radical, an alkoxy radical, an alkoxyalkyl radical, a carbamoyl radical, an alkylcarbamoylradical, a hydroxyalkylcarbamoyl radical, an amido radical, an alkylamido radical, an alkylcarbonyl radical, an alkoxycarbonyl radical, an aryloxy radical, an acyloxy radical, an alkylthio radical, an arylthio radical, a heteroarylthio radical, a heteroaryloxy radical, a 5- or 6-membered heterocycle having at least one nitrogen, oxygen or sulfur atom, which is optionally substituted, an aryl radical, which is optionally substituted, a sulfonyl radical, a sulfinyl radical, a phosphonyl radical, a sulfamoyl radical, a siloxy radical, an acyloxy radical, a carbamoyloxy radical, a sulphonamide radical, an imide radical, an ureido radical, a sulfamoylamino radical, an alkoxycarbonylamino radical, an aryloxycarbonylamino radical, an aryloxycarbonyl radical, and a benzenesulfonamido radical.

7. A method of dyeing keratin fibers comprising use of a 3-halo-1H-indol-4-amine compound, as a coupler;

wherein the 3-halo-1H-indol-4-amine compound is a compound of general formula (I)

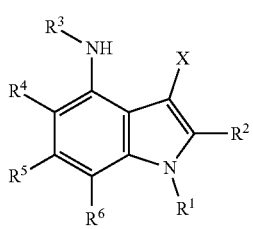

(I)

wherein radical X is a halogen atom selected from the group consisting of chlorine or bromine;

wherein radicals $R^1$ and $R^3$ are the same or different and are selected from the group consisting of:
  (a) N-linked monovalent substituents selected from the group consisting of:
    (i) substituted or unsubstituted, straight or branched, alkyl, mono- or poly-unsaturated alkyl, heteroalkyl, aliphatic, heteroaliphatic, or heteroolefinic systems;
    (ii) substituted or unsubstituted, mono- or polycyclic aliphatic;
    (iii) an aromatic ring or 5- or 6-membered heteroaromatic rings having at least one nitrogen, oxygen or sulfur atom; and,
    (iv) substituted or unsubstituted, mono- or polyhydroxy-, mono- or polyamino-, mono- or polyfluoro-alkyl systems, or mixtures thereof; wherein said systems of (i) and (ii) comprise from about 1 to about 10 carbon atoms and from about 0 to about 5 heteroatoms selected from the group consisting of O, S, N, P, and Si;
  (b) hydrogen;
  (c) a linker group (L) between one of the radical $R^1$ or $R^3$ of a first compound of formula (I) and between one of the radical $R^1$ or $R^3$ of a second compound of formula (I), both compounds forming therefore a dimeric structure, wherein the linker group is of general formula (L)

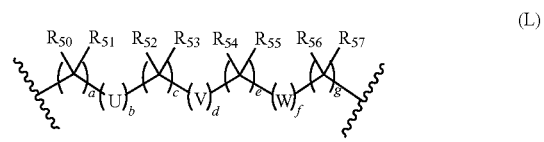

(L)

wherein
  (i) a, c, e and g are each independently an integer from 0 to 3, provided that the sum of a, c, e and g is greater than or equal to 2; b, d and f are each independently 0 or 1; and $R_{50}$, $R_{51}$, $R_{52}$, $R_{53}$, $R_{54}$, $R_{55}$, $R_{56}$ and $R_{57}$ are each independently hydrogen or $C_1$-$C_2$ alkyl group;
  (ii) U is an aromatic ring, alkenyl or alkynyl moiety;
  (iii) V is O, N or S; and
  (iv) W is a cyclic aliphatic ring;
wherein radicals $R^2$ and $R^5$ are the same or different and are selected from the group consisting of:
  (a) C-linked monovalent substituents selected from the group consisting of:
    (i) substituted or unsubstituted, straight or branched, alkyl, mono- or poly-unsaturated alkyl, heteroalkyl, aliphatic, heteroaliphatic, or heteroolefinic systems;
    (ii) substituted or unsubstituted, mono- or polycyclic aliphatic;
    (iii) halogen atom;
    (iv) a boronic acid group, a boronic ester group;
    (v) an aromatic ring or 5- or 6-membered heteroaromatic rings having at least one nitrogen, oxygen or sulfur atom; and,
    (vi) substituted or unsubstituted, mono- or polyhydroxy-, mono- or polyamino-, mono- or polyfluoro-alkyl systems, or mixtures thereof; wherein said systems of (i) and (ii) comprise from about 1 to about 10 carbon atoms and from about 0 to about 5 heteroatoms selected from the group consisting of O, S, N, P, and Si;
  (b) S-linked monovalent substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;
  (c) O-linked monovalent substituents selected from the group consisting of $OA^1$, and $ONA^1A^2$;
  (d) N-linked monovalent substituents selected from the group consisting of $NA^1A^2$, $(NA^1A^2A^3)^+$, $NA^1OA^2$, $NA^1SA^2$, $N=NA^1$, $N=NOA'$, $NA^1CN$, and $NA^1NA^2A^3$;
  (e) monovalent substituents selected from the group consisting of $COOA^1$, $CONA^1{}_2$, $CONA^1COA^2$, and $C(=NA^1)NA^1A^2$;
  (f) fluoroalkyl monovalent substituents selected from the group consisting of mono-, poly-, and per-fluoro alkyl systems comprising from about 1 to about 12 carbon atoms and from about 0 to about 4 heteroatoms; and
  (g) hydrogen;
wherein $A^1$, $A^2$, and $A^3$ are monovalent and are independently selected from the group consisting of: H; substituted or unsubstituted, straight or branched, alkyl, mono- or poly-unsaturated alkyl, heteroalkyl, aliphatic, heteroaliphatic, or heteroolefinic systems; substituted or unsubstituted, mono- or poly-cyclic aliphatic, aryl, or heterocyclic systems; and substituted or unsubstituted, mono-, poly-, per-fluoro alkyl systems or $A^1$ and $A^2$ together with nitrogen atom to which they are bound form a ring; wherein said systems comprise from about 1 to about 10 carbon atoms and from about 0 to about 5 heteroatoms selected from the group consisting of O, S, N, P, and Si;

wherein one of radicals $R^2$ or $R^4$ is selected from the group consisting of a hydrogen atom and/or a nucleofuge group;

wherein the other radical $R^4$ or $R^2$ or is selected from the group consisting of:
(a) C-linked monovalent substituents selected from the group consisting of:
  (i) substituted or unsubstituted, straight or branched, alkyl, mono- or poly-unsaturated alkyl, heteroalkyl, aliphatic, heteroaliphatic, or heteroolefinic systems;
  (ii) substituted or unsubstituted, mono- or polycyclic aliphatic;
  (iii) halogen atom;
  (iv) a boronic acid group, a boronic ester group;
  (v) an aromatic ring or 5- or 6-membered heteroaromatic rings having at least one nitrogen, oxygen or sulfur atom; and,
  (vi) substituted or unsubstituted, mono- or polyhydroxy-, mono- or polyamino-, mono- or polyfluoro-alkyl systems, or mixtures thereof; wherein said systems of (i) and (ii) comprise from about 1 to about 10 carbon atoms and from about 0 to about 5 heteroatoms selected from the group consisting of O, S, N, P, and Si;
(b) S-linked monovalent substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;
(c) O-linked monovalent substituents selected from the group consisting of $ONA^1A^2$;
(d) monovalent substituents selected from the group consisting of $COOA^1$, $CONA^1{}_2$, $CONA^1COA^2$, $C(=NA^1)NA^1A^2$, and CN;
(e) fluoroalkyl monovalent substituents selected from the group consisting of mono-, poly-, and per-fluoro alkyl systems comprising from about 1 to about 12 carbon atoms and from about 0 to about 4 heteroatoms; and
(f) hydrogen;
wherein $A^1$, $A^2$, and $A^3$ are monovalent and are independently selected from the group consisting of: H; substituted or unsubstituted, straight or branched, alkyl, mono- or poly-unsaturated alkyl, heteroalkyl, aliphatic, heteroaliphatic, or heteroolefinic systems; substituted or unsubstituted, mono- or poly-cyclic aliphatic, aryl, or heterocyclic systems; and substituted or unsubstituted, mono-, poly-, per-fluoro alkyl systems or $A^1$ and $A^2$ together with nitrogen atom to which they are bound form a ring; wherein said systems comprise from about 1 to about 10 carbon atoms and from about 0 to about 5 heteroatoms selected from the group consisting of O, S, N, P, and Si;
and their salts thereof.

8. A hair dyeing composition comprising:
(a) a coupler being a 4-amino-indole compound of formula (I), according to claim 1;
(b) a developer; and
(c) an oxidizing agent.

9. A hair dyeing composition, according to claim 8, wherein the composition comprises from 0.005% to 5% of a coupler being a 4-amino-indole compound of formula (I), by weight of the total composition.

10. A hair dyeing composition, according to claim 8, wherein the composition comprises from 0.005% to 5% of a developer, by weight of the total composition.

11. A hair dyeing composition, according to claim 8, wherein the composition comprises from 0.1% to 3% of an oxidizing agent, by weight of the total composition.

12. A hair dyeing composition, according to claim 8, wherein the developer is selected from the group consisting of a pyrazole derivative, a p-phenylenediamine derivative, a p-aminophanol derivatives, their physiologically compatible water-soluble salts, or combinations thereof.

13. A hair dyeing composition, according to claim 8, wherein the pyrazole derivative is a compound of general formula (V)

(V)

wherein radical $R^7$ is selected from the group consisting of hydrogen, a saturated $(C_1-C_6)$-alkyl group, an unsaturated $(C_2-C_6)$-alkyl group, a $(C_2-C_6)$-hydroxyalkyl group, a $(C_3-C_6)$-polyhydroxyalkyl group, a $(C_1-C_6)$-alkoxy-$(C_2-C_6)$-alkyl group, a substituted or unsubstituted benzyl group, a substituted or unsubstituted phenyl group, a substituted or unsubstituted 5- or 6-membered heteroaryl group, a substituted or unsubstituted thiazolylmethyl group, a quaternary group $Q^+$ linked to the pyrazole ring via a $(C_1-C_2)$-alkylene diradical or a phenylene diradical, wherein $Q^+$ represents (a) a quaternary trialkylammonium, wherein the alkylgroups may be identical or different and, independently of one another, are a saturated or unsaturated $(C_1-C_{12})$-alkyl group; or (b) an aromatic substituted or unsubstituted 4- to 6-membered heterocyclic quaternary ammonium group, which may contain other heteroatoms like nitrogen, sulfur or oxygen, with the proviso that the cationic heterocycle comprises at most three heteroatoms, where the heterocycle has at most one sulfur atom or oxygen atom and the benzocondensed form of these 4- to 6-membered heterocyclic quaternary ammonium group;

or group between the radical $R^7$ of a first compound of formula (V) and between the radical $R^7$ of a second compound of formula (V), both compounds forming therefore a dimeric structure, wherein the linker group is of general formula (VI)

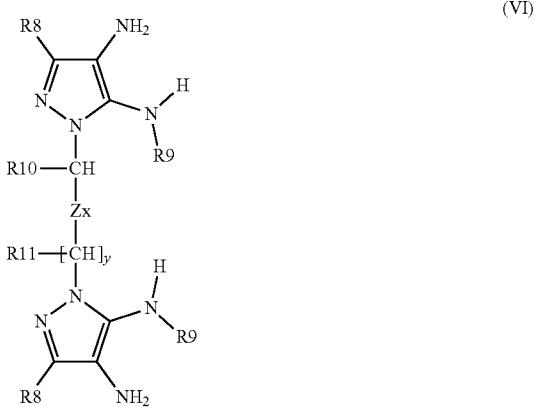

(VI)

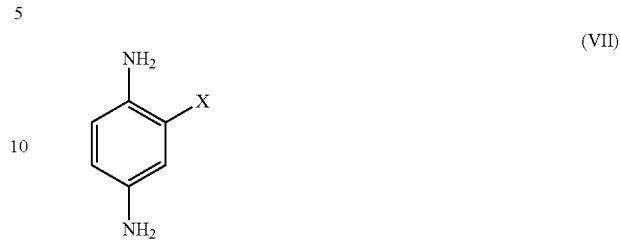

(VII)

wherein radical $R^8$ is selected from the group consisting of hydrogen, a saturated $(C_1$-$C_6)$-alkyl group, an unsaturated $(C_2$-$C_6)$-alkyl group, a $(C_2$-$C_6)$-hydroxyalkyl group, a $(C_2$-$C_6)$-aminoalkyl group, a $(C_1$-$C_4)$-alkylamino-$(C_1$-$C_4)$-alkyl group, a di$(C_1$-$C_4)$-alkylamino-$(C_1$-$C_4)$-alkyl group, a substituted or unsubstituted benzyl group, a $C_1$-$C_6$ alkoxyl group, a substituted or unsubstituted phenoxyl or aryloxyl group, a substituted or unsubstituted aryl or heteroaryl group, a carboxylic acid group, a carboxylic acid ester group, a carboxamide group, a nitrile group, or $R^8$ of a first compound is linked with R;

wherein radical $R^9$ is selected from the group consisting of hydrogen, a saturated $(C_1$-$C_6)$-alkyl group, an unsaturated $(C_2$-$C_6)$-alkyl group, a $(C_2$-$C_6)$-hydroxyalkyl group, a $(C_3$-$C_6)$-dihydroxyalkyl group, a $(C_1$-$C_4)$-alkoxy-$(C_1$-$C_4)$-alkyl group or a benzyl group;

radicals $R^{10}$ and $R^{11}$, independently of each other, are the same or different and each represent hydrogen, a saturated $(C_1$-$C_6)$-alkyl group, an unsaturated $(C_2$-$C_6)$-alkyl group, a $(C_2$-$C_6)$-hydroxyalkyl group, an hydroxy group, an aryl group, an heteroaryl group, a carboxylic acid group, a carboxylic ester group, a substituted or unsubstituted carboxylic amide group, or $R^{10}$ and $R^{11}$ together represent an unsubstituted or substituted $(C_1$-$C_6)$-alkylene group;

wherein radical Z represents a $(C_1$-$C_{10})$-alkyl diradical, which is optionally interrupted by an heteroatom, for example a nitrogen, an oxygen or a sulfur atom, an aromatic or heteroaromatic diradical, which may be substituted optionally with a hydroxyl group or a $(C_1$-$C_6)$-alkyl group and/or may be subjected to a benzocondensation once or twice; or a diradical of formula —Ar(Alk)$_n$-Ar—, wherein Ar represents an arylene group or a heteroarylene group, which may optionally be substituted, Alk represents a —CH2- group and n represents a number from 0 to 6; and x and y independently of each other represents 0 or 1.

14. A hair dyeing composition, according to claim 8, wherein the pyrazole derivative is selected from the group consisting of 1-methyl-1H-pyrazole-4,5-diamine, 2-(4,5-diamino-1H-pyrazol-1-yl)ethanol, 1-isopropyl-1H-pyrazole-4,5-diamine, 1-(4-methylbenzyl)-1H-pyrazole-4,5-diamine, 1-(benzyl)-1H-pyrazole-4,5-diamine, 1-(4-chlorobenzyl)-1H-pyrazole-4,5-diamine, 1-(heptyl)-1H-pyrazole-4,5-diamine, 1-(pentyl)-1H-pyrazole-4,5-diamine, 1-(hexyl)-1H-pyrazole-4,5-diamine, their physiologically acceptable salts thereof, or mixtures thereof.

15. A hair dyeing composition, according to claim 12, wherein the p-phenylenediamine derivative is a compound of general formula (VII)

wherein radical X is selected from the group consisting of:
(a) a hydrogen,
(b) a $C_1$-$C_6$ alkyl;
(c) methoxy, ethoxy, propoxy, isopropoxy or butoxy;
(d) $C_1$-$C_6$ alkyl with hydroxy substitution;
(e) —(CH$_2$)$_y$—O—CH$_3$; y being from 1-3;
(f) —(CH$_2$)$_y$—O—CH$_2$CH$_3$; y being from 1-3;
(g) —(CH$_2$)$_y$—O—CH$_2$CH$_2$CH$_3$; y being from 1-3;
(h)

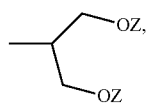

Z being hydrogen or $C_{1-3}$ alkyl;
and mixtures thereof.

16. A hair dyeing composition, according to claim 12, wherein the p-aminophenol derivative is a compound of formula (VIII)

(VIII)

wherein radical X is selected from the group consisting of:
(a) a hydrogen
(b) a $C_1$-$C_6$ alkyl radical;
(c) methoxy, ethoxy, propoxy, isopropoxy or butoxy;
(d) $C_1$-$C_6$ alkyl radical with hydroxy substitution;
(e) —(CH$_2$)$_y$—O—CH$_3$; y is from 1-3;
(f) —(CH$_2$)$_y$—O—CH$_2$CH$_3$; y is from 1-3;
(g) —(CH$_2$)$_y$—O—CH$_2$CH$_2$CH$_3$; y is from 1-3;
(h)

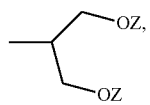

Z is hydrogen or $C_{1-3}$ alkyl radical;
and mixtures thereof;
wherein the substitutions of the X moiety can be on the 2 or the 3 position of the benzene ring.

17. A hair dyeing composition, according to claim 8, wherein it comprises further additional compounds, the additional compounds being selected from the group consisting of a solvent, an alkalizing agent, an additional oxidative dye precursor, a direct dye, a chelant, a radical scavenger, a pH modifier and/or a buffering agent, a thickener and/or a rheology modifier, a salt, a carbonate ion source, a conditioning agent, a surfactant, and their combinations thereof.

18. A method for dyeing hair, comprising the following steps:
   (a) providing a tint composition comprising a coupler being a 4-amino-indole compound of formula (I), according to claim 7; and, a developer;
   (b) providing an oxidizing composition comprising an oxidizing agent;
   (c) combining the tint composition and the oxidizing composition to form a hair dyeing composition;
   (d) contacting hair with the hair dyeing composition.

19. A hair dyeing kit, comprising:
   (a) an individually packaged oxidizing composition comprising an oxidizing agent;
   (b) an individually packaged tint composition comprising a coupler being a 4-amino-indole compound of formula (I), according to claim 7; and, a developer.

* * * * *